US007291737B2

(12) United States Patent
Kuhar et al.

(10) Patent No.: US 7,291,737 B2
(45) Date of Patent: *Nov. 6, 2007

(54) COCAINE RECEPTOR BINDING LIGANDS

(75) Inventors: Michael J. Kuhar, Baltimore, MD (US); Frank I. Carroll, Durham, NC (US); John W. Boja, Baltimore, MD (US); Anita H. Lewin, Chapel Hill, NC (US); Philip Abraham, Cary, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/986,352

(22) Filed: Nov. 12, 2004

(65) Prior Publication Data

US 2005/0197360 A1     Sep. 8, 2005

Related U.S. Application Data

(63) Continuation of application No. 10/279,851, filed on Oct. 25, 2002, now Pat. No. 7,189,737, which is a continuation of application No. 08/706,263, filed on Sep. 4, 1996, now Pat. No. 6,531,483, which is a continuation-in-part of application No. 08/506,541, filed on Jul. 24, 1995, now abandoned, which is a continuation-in-part of application No. 08/436,970, filed on May 8, 1995, now Pat. No. 5,736,123, and a continuation-in-part of application No. 08/164,576, filed on Dec. 10, 1993, now Pat. No. 5,496,953, which is a continuation-in-part of application No. 07/972,472, filed on Mar. 23, 1993, now Pat. No. 5,413,779, which is a continuation-in-part of application No. 07/792,648, filed on Nov. 15, 1991, now Pat. No. 5,380,848, and a continuation-in-part of application No. PCT/US91/05553, filed on Aug. 7, 1991, which is a continuation-in-part of application No. 07/564,755, filed on Aug. 9, 1990, now Pat. No. 5,128,118.

(51) Int. Cl.
C07D 451/02 (2006.01)

(52) U.S. Cl. .................................................. 546/124

(58) Field of Classification Search ................. 546/124
See application file for complete search history.

(56) References Cited

U.S. PATENT DOCUMENTS

| 3,133,073 | A | 5/1964 | Archer |
|---|---|---|---|
| 3,813,404 | A | 5/1974 | Clark |
| 3,975,237 | A | 8/1976 | Rubenstein et al. |
| 4,041,040 | A | 8/1977 | Christenson et al. |
| 4,179,567 | A | 12/1979 | Clark et al. |
| 4,235,864 | A | 11/1980 | Kaul et al. |
| 4,366,154 | A | 12/1982 | Tomesch |
| 5,122,361 | A | 6/1992 | Kung |
| 5,128,118 | A | 7/1992 | Carroll et al. |
| 5,141,959 | A | 8/1992 | Carroll et al. |
| 5,186,921 | A | 2/1993 | Kung et al. |
| 5,262,428 | A | 11/1993 | Davies et al. |
| 5,288,872 | A | 2/1994 | Davies et al. |
| 5,310,912 | A | 5/1994 | Neumeyer et al. |
| 5,374,636 | A | 12/1994 | Moldt |
| 5,380,848 | A | 1/1995 | Kuhar et al. |
| 5,413,779 | A | 5/1995 | Kuhar et al. |
| 5,439,666 | A | 8/1995 | Neumeyer et al. |
| 5,496,953 | A | 3/1996 | Kuhar et al. |
| 5,554,626 | A | 9/1996 | Moldt |
| 5,736,123 | A | 4/1998 | Carroll |
| 5,831,095 | A | 11/1998 | Gonzalez et al. |
| 5,935,953 | A | 8/1999 | Kuhar et al. |
| 6,123,917 | A | 9/2000 | Carroll |
| 6,329,520 | B1 | 12/2001 | Carroll et al. |
| 6,358,492 | B1 | 3/2002 | Kuhar et al. |
| 6,416,735 | B1 | 7/2002 | Carroll et al. |
| 6,479,509 | B1 | 11/2002 | Carroll |
| 6,531,481 | B2 | 3/2003 | Carroll et al. |
| 6,531,483 | B1 | 3/2003 | Kuhar et al. |
| 6,538,010 | B1 | 3/2003 | Carroll |
| 6,552,032 | B2 | 4/2003 | Carroll et al. |

(Continued)

FOREIGN PATENT DOCUMENTS

WO    WO93/09814    5/1993

OTHER PUBLICATIONS

U.S. Appl. No. 11/272,492, filed Nov. 14, 2005, Carroll.

(Continued)

*Primary Examiner*—Celia Chang
(74) *Attorney, Agent, or Firm*—Oblon, Spivak, McClelland, Maier & Neustadt, P.C.

(57) ABSTRACT

A class of binding ligands for cocaine receptors and other receptors in the brain. Specifically, a novel family of compounds shows high binding specificity and activity, and, in a radiolabeled form, can be used to bind to these receptors, for biochemical assays and imaging techniques. Such imaging is useful for determining effective doses of new drug candidates in human populations. In addition, the high specificity, slow onset and long duration of the action of these compounds at the receptors makes them particularly well suited for therapeutic uses, for example as substitute medication for psychostimulant abuse. Some of these compounds may be useful in treating Parkinson's Disease or depression, by virtue of their inhibitory properties at monoamine transporters.

2 Claims, 3 Drawing Sheets

U.S. PATENT DOCUMENTS

| | | | |
|---|---|---|---|
| 6,559,159 | B2 | 5/2003 | Carroll et al. |
| 6,593,348 | B2 | 7/2003 | Carroll et al. |
| 6,706,880 | B2 | 3/2004 | Carroll et al. |
| 6,900,228 | B1 | 5/2005 | Carroll et al. |
| 7,011,813 | B2 * | 3/2006 | Kuhar et al. ............... 424/1.85 |
| 2002/0132828 | A1 | 9/2002 | Carroll et al. |
| 2002/0188003 | A1 | 12/2002 | Kuhar et al. |
| 2003/0158415 | A1 | 8/2003 | Carroll et al. |
| 2003/0176434 | A1 | 9/2003 | Carroll |
| 2003/0203934 | A1 | 10/2003 | Kuhar et al. |
| 2004/0146518 | A1 | 7/2004 | Carroll et al. |
| 2005/0197360 | A1 | 9/2005 | Kuhar et al. |

OTHER PUBLICATIONS

Canadian Office Action mailed dated 20, 2005.

Maarten E. A. Reith et al., "Structural Requirements for Cocaine Congeners to Interact with Dopamine and Serotonin Uptake Sites in Mouse Brain and to Induce Stereotyped Behavior", Biochemical Pharmacology, vol. 35, No. 7, pp. 1123-1129, 1986.

Australian Office Action Dated Jan. 25, 2000, 2pp.

PCT Written Opinion Dated Jul. 24, 1998, 5pp.

Australian Patent Office Examiner's first report received in corresponding application on Feb. 4, 2003.

J. Med. Chem. (JMCMAR, 00222623), Mar. 20, 1992, vol. 35(6), pp. 969-981, XP002116827, Research Triangle Inst., Research Triangle Park, 27709, North Carolina, USA.

Nida Res. Monogr. (MIDAD4, 03618595), 1990, vol. 96 (Drugs Abuse: Chem., Pharmacol., Immunol., AIDS), pp. 112-121, XP002116828, Research Triangle Inst., Research Triangle Park, 27709, North Carolina, USA.

J. Med. Chem. (JMCMAR, 00222623), 1993, vol. 36(20), pp. 2886-2890, XP002116829, Research Triangle Inst., Research Triangle Park, 27709, North Carolina, USA.

F. Carroll, et al., "Synthesis and ligand binding of 3,beta.-(3-substituted phenyl)-and 3.beta.-(3-4-disubstituted phenyl)tropane-2.beta.-carboxylic acid methyl esters", Med. Chem. Res. (MCREEB, 10542523), 1991, vol. 1(6), pp. 382-387, XP002116826, Research Triangle Inst., Research Triangl Park, 27709, North Carolina, USA.

J.L. Neumeyer et al., "[$^{123}$I]-2β-Carbomethoxy-3β-(4-iodophenyl)tropane: High-Affinity SPECT Radiotracer of Monoamine Reuptake Siters in Brain[1]", Journal of Medicinal Chemistry, vol. 34, No. 10, Oct. 1991, pp. 3144-3146.

F.I. Carroll, "Synthesis Ligand Binding, QSAR, and CoMFA study of 3β-(p-Substituted phenyl)tropane-2β-carboxylic Acid Methyl Esters", Journal of Medicinal Chemistry, vol. 34, No. 9, Sep. 1991, pp. 2719-2725.

Chemical Abstracts, vol. 114, No. 7, Feb. 18, 1991, Abstract No. 62429c, T.M. Naseree et al., "Synthesis for tritium-labeled (3H)WIN 35, 065-02; A New Radioligand for Cocaine Receptors".

F.I. Carroll, et al., "Isopropyl and phenyl esters of 3-beta-(4-substituted phenyl)tropan-2-beta-carboxyl acids", Journal of Medicinal Chemistry, vol. 35, No. 16, Jun. 26, 1992, pp. 2497-2500.

Bojia, et al., "High Potency Cocaine Analogs: Neurochemical, Imaging and Behavioral Studies", The Neurobiology of Drug and Alcohol Addiction, Annauls of the New York Academy of Sciences, vol. 654, Jun. 28, 1992.

Balaster, et al., "Potent substituted-3β-phenltropane analogs of cocaine have cocaine-like discriminative stimulus effects", Drug and Alcohol Dependence, 29 (1991), pp. 145-151, Elsevier Scientific Publishers Ireland Ltd.

Cline, et al., "Stimulus generalization from cocaine to analogs with high in vitro affinity for dopamine uptake sites", Behavioural Pharmacology (1992), 3, pp. 113-116 Short Report.

Cline, et al., "Behavioral Effects of Novel Cocaine Analogs: A Comparison with in Vivo Receptor Binding Potency [1,2]", The Journal of Pharmocology and Experimental Therapeutics, vol. 260, No. 3, pp. 1174-1179.

* cited by examiner

COCAINE RECEPTOR BINDING LIGANDS

CONTINUING APPLICATION INFORMATION

This application is a Continuation of U.S. application Ser. No. 10/279,851, filed on Oct. 25, 2002, now U.S. Pat. No. 7,189,737, which is a Continuation of U.S. application Ser. No. 08/706,263, filed on Sep. 4, 1996, now U.S. Pat. No. 6,531,483, which is a Continuation-In-Part of U.S. application Ser. No. 08/506,541, filed on Jul. 24, 1995, abandoned, which is a Continuation-in-Part of U.S. application Ser. No. 08/436,970, filed on May 8, 1995, now U.S. Pat. No. 5,736,123 and a Continuation-in-Part of U.S. application Ser. No. 08/164,576, filed on Dec. 10, 1993, now U.S. Pat. No. 5,496,953. U.S. application Ser. No. 08/436,970 is a Continuation-in-Part of U.S. application Ser. No. 08/164,576, which is a Continuation-in-Part of U.S. application Ser. No. 07/972,472, filed on Mar. 23, 1993, now U.S. Pat. No. 5,413,779, and a which is a Continuation-in-part of U.S. application Ser. No. 07/792,648, filed on Nov. 15, 1991, now U.S. Pat. No. 5,380,848 and a Continuation-in-part of International Application No. PCT/US91/05553, filed on Aug. 7, 1991, which is a Continuation-in-part of U.S. application Ser. No. 07/564,755 filed on Aug. 9, 1990, now U.S. Pat. No. 5,128,118, all of which are incorporated herein by reference.

FIELD OF THE INVENTION

This invention is directed to a class of binding ligands for cocaine receptors and other receptors in the brain. Specifically, a novel family of compounds shows high binding specificity and activity, and, in a radiolabeled form, can be used to bind to these receptors, for biochemical assays and imaging techniques. Such imaging is useful for determining effective doses of new drug candidates in human populations. In addition, the high specificity, slow onset and long duration of the action of these compounds at the receptors makes them particularly well suited for therapeutic uses, for example as substitute medication for psychostimulant abuse. Some of these compounds may be useful in treating Parkinson's Disease or depression, by virtue of their inhibitory properties at monoamine transporters.

DISCLOSURE OF PARENT APPLICATIONS

This application claims priority, inter alia, from of U.S. patent application Ser. No. 07/972,472 filed Mar. 23, 1993, now. U.S. Pat. No. 5,413,779, the entirety of which is incorporated by reference. This application also claims priority from U.S. patent application Ser. No. 07/564,755, now U.S. Pat. No. 5,128,118, and U.S. PCT Application PCT/US91/05553 (the U.S. National Phase of which is U.S. Ser. No. 07/972,472.), filed Aug. 9, 1991, both applications being incorporated herein by reference. In U.S. application Ser. No. 07/564,755, there is disclosure of a family of compounds exhibiting particularly high specificity and affinity for cocaine receptors and other neurotransmitter receptors in the brain of the formula:

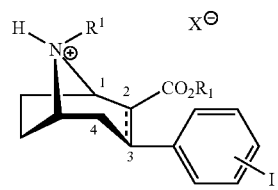

Where the broken line represents an optional chemical bond and the substituents at 2 and 3 may be at any position;

The iodo substituent may be at o, m, p, or multisubstituted;

$R_1 = CH_3$, $CH_2CH=CH_2$, $(CH_2)_n C_6 H_5$ n=1-4;

$R_2 = CH_3$, $C_2H_5$, $CH_3(CH_2)_3$, $(CH_3)_2 CH$, $C_6 H_5$, $C_6 H_5 CH_2$, $C_6 H_5 (CH_2)_2$;

X=pharmacologically acceptable anion

Sites of Specific Interest Included Cocaine Receptors Associated with Dopamine (DA) Transporter Sites.

Subsequently, in the U.S. PCT Application from which priority is claimed, and which is incorporated herein by reference, the values for $R_1$ and $R_2$ were expanded, such that $R_1$ may be an alkyl of 1-7 carbon atoms, $CH_2 CR_3 = CR_4 R_5$ wherein $R_3$-$R_5$ are each, independently $C_{1-6}$ alkyl, or phenyl compounds of the formula $C_6 H_5 (CH_2)_y$, wherein y=1-6. The PCT filing also reveals the affinity of these compounds for cocaine receptors associated with serotonin (5-hydroxytryptamine, 5-HT) transporters, and confirms, for the first time, that the in vitro binding reported in the earlier-filed application, is confirmed in in vivo testing. Specific disclosure for a variety of applications, including using the compounds in both PET and SPECT scanning, wherein either the iodine substituent, or one of the carbon groups is radioactive (I-123, 125 or 131 and C11) thus providing methods for scanning for the presence of specific cocaine receptors. Such scanning processes may be used to determine physiological conditions associated with dopamine and serotonin reuptabe inhibitors, which lead to behavioral and neurodegenerative disorders/diseases. Such disorders include depression, bipolar disorder, eating disorders, obesity, attention deficit disorder, panic attacks and disorders, obsessive-compulsive disorder, Parkinson's Disease, and cocaine, nicotine and alcohol addiction. These compounds, in addition to being used in treatment of these disorders, may be used to examine in general the density and distribution of specific cocaine receptors in various parts of the brain and/or body, to determine the efficacy of neurological treatments aimed at halting or reversing the degeneration of specific nerves in the brain, and for screening drugs, such as antidepressant drugs.

The affinity and specificity of these compounds, as reported in the applications incorporated, is surprisingly high, and compared with prior art compounds, such as [³H]WIN 35,428, the novel compounds of these applications exhibit extremely low $IC_{50}$ values for binding inhibition.

In U.S. patent application Ser. No. 08/506,541, filed Jul. 24, 1995 Dec. 10, 1993, also incorporated herein by reference in its entirety, a family of compounds was disclosed, having the formula:

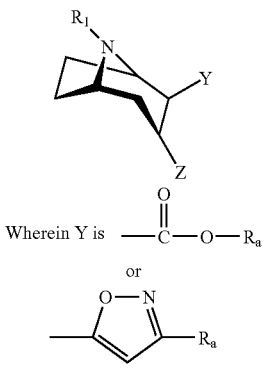

Wherein Y is —C(=O)—O—$R_a$ or

[isoxazole]—$R_a$

Wherein
$R_1$ is hydrogen, $C_{1-5}$ alkyl
$R_a$ is phenyl, $C_{1-6}$ alkyl, $C_{1-6}$ alkyl-substituted phenyl
$R_b$ is $C_{1-6}$ alkyl, phenyl, $C_{1-6}$ alkyl substituted phenyl and
Z is phenyl or naphtyl bearing 1-3 substituents selected from the group consisting of F, Cl, I, and $C_{1-6}$ alkyl.

These compounds exhibit unusually high affinity and specificity for binding to receptors for the dopamine transporter site, as well as the serotonin transporter site, based on inhibition of [$^3$H]paroxetine binding. This high affinity makes certain of these compounds particularly well suited for use as therapeutic agents, as well as for imaging agents for dopamine and serotonin transporters.

SUMMARY OF THE INVENTION

Accordingly, one object of this invention is to provide novel compounds which bind to cocaine receptors.

Another object of the invention is to provide novel 3-(substituted phenyl)-2-(substituted)tropane analogs which bind to cocaine receptors.

Still another object of the invention is to provide 3-(substituted phenyl)-2-(substituted)tropane analogs which bind preferentially to the dopamine transporter.

Yet another object of the invention is to provide 3-(substituted phenyl)-2-(substituted)tropane analogs which bind preferentially to the serotonin transporter.

Another object of the invention is to provide a compound of the formula

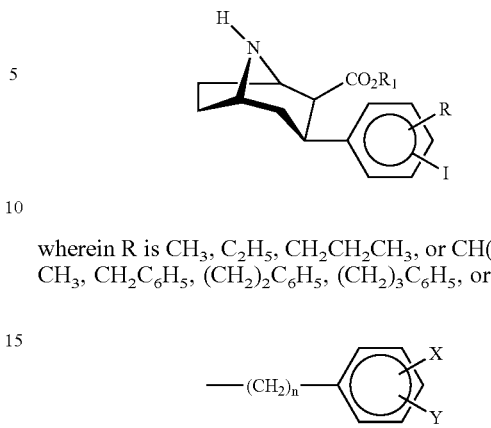

wherein R is $CH_3$, $C_2H_5$, $CH_2CH_2CH_3$, or $CH(CH_3)_2$, $R_1$ is $CH_3$, $CH_2C_6H_5$, $(CH_2)_2C_6H_5$, $(CH_2)_3C_6H_5$, or

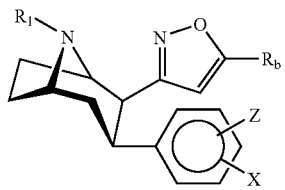

wherein X is H, $OCH_3$, or Cl and Y is H, $OCH_3$, or Cl, and n=1-8.

Another object of the invention is to provide compounds having the following formulas:

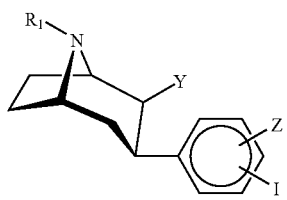

wherein
$R_1$=hydrogen, $C_{1-5}$ alkyl,
X=H, $C_{1-6}$ alkyl, $C_{3-8}$ cycloalkyl, $C_{1-4}$ alkoxy, $C_{1-6}$ alkynyl, halogen, amino, acylamido, and
Z=H, I, Br, Cl, F, CN, $CF_3$, $NO_2$, $N_3$, $OR_1$, $CONH_2$, $CO_2R_1$, $C_{1-6}$ alkyl, $NR_4R_5$, $NHCOR_5$, $NHCO_2R_6$,
$R_b$ is $C_{1-6}$ alkyl, phenyl, $C_{1-6}$ alkyl substituted phenyl

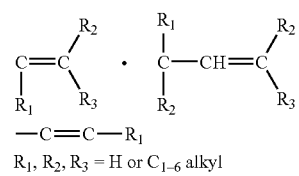

R, Y, and Z are as defined above
and Z may additionally be $C(R_1)=C(R_2)(R_3)$ · $C(R_1)(R_2)—CH=C(R_2)(R_3)$

—C≡C—$R_1$ $R_1$, $R_2$, $R_3$ = H or $C_{1-6}$ alkyl

-continued

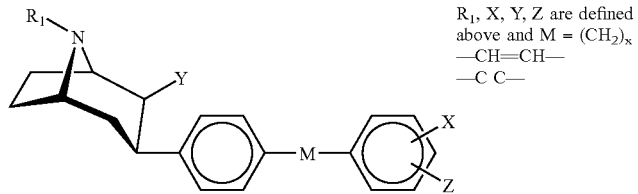

R₁, X, Y, Z are defined
above and M = $(CH_2)_x$
—CH=CH—
—C C—

A further object of the invention is to provide a method for treating psychostimulant abuse, by administering to a patient in need of such treatment a pharmaceutically effective amount of a 3-(substituted phenyl)-2-(substituted)tropane analog.

A still further object of the invention is to provide method for inhibiting the action of a psychostimulant, by administering to a patient in need of such treatment a psychostimulant-inhibiting amount of a 3-(substituted phenyl)-2-(substituted)tropane analog.

Still another object of the invention is to provide a method for inhibiting neurotransmitter re-uptake by administering to a patient in need of such treatment a neurotransmitter transporter-inhibiting amount of a 3-(substituted phenyl)-2-(substituted)tropane analog.

Another object of the invention is to provide a method for treating neurodegenerative disorders, by administering to a patient in need of such treatment a pharmaceutically effective amount of a 3-(substituted phenyl)-2-(substituted)tropane analog.

Still another object of the invention is to provide a method for treating depression, by administering to a patient in need of such treatment a pharmaceutically effective amount of a 3-(substituted phenyl)-2-(substituted)tropane analog.

Briefly, the invention pertains to the discovery that certain cocaine analogs are particularly well suited for therapeutic use as neurochemical agents. These particular cocaine analogs, in modulating neurotransmitter actions, may also be useful for modulating the actions of pyschostimulant drugs, for modulating endocrine function, for modulating motor function, and for modulating complex behaviors.

With the foregoing and other objects, advantages and features of the invention that will become here in after apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The present invention includes novel compounds having the following formula:

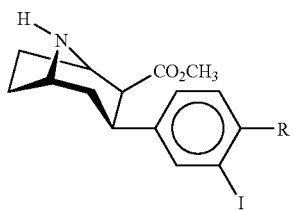

1a, R = $C_2H_3$
b, R = $CH_2CH_2CH_3$
c, R = $CH(CH_3)_2$

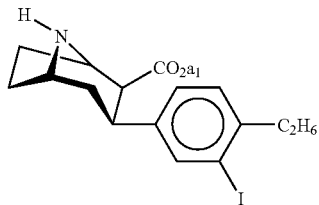

2a, R = $CH_2C_2H_6$
b, R = $(CH_2)_2C_2H_6$
c, R = $(CH_2)_3C_2H_6$

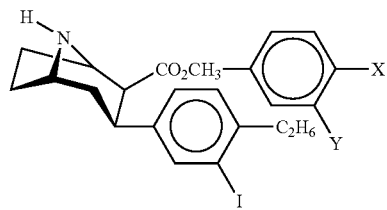

3a, X = H, Y = $OCH_3$
b, X = $OCH_3$, Y = H
c, X = $OCH_3$, Y = $OCH_3$
d, X = Cl, Y = H
e, X = H, Y = Cl
f, X = Cl, Y = Cl

The compounds of this invention can be prepared according to the synthesis methods described in the parent applications. Alternative synthesis for related compounds will be apparent to those of ordinary skill in the art. Particular synthesis schemes are exemplified in U.S. Pat. No. 5,444,070, which is incorporated herein in its entirety. Additional schemes follow hereinbelow.

Preparation of 3β-(Substituted phenyl)tropane-2β-heterocyclic Analogues

Chemistry

Figure 1:
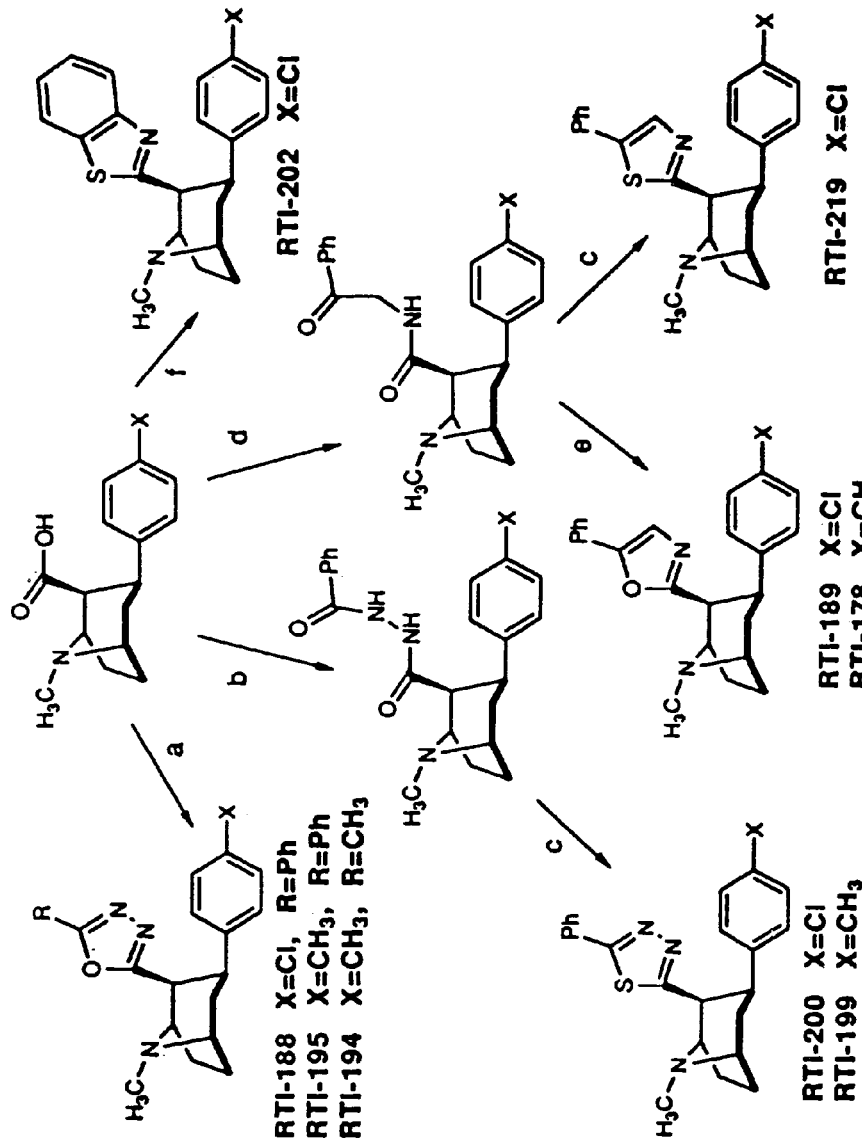
FIG. 1 depicts the scheme for converting 3-(substituted phenyl)-2-tropane carboxylic acid (tropane acid) to 2-substituted tetrazoles, oxazoles, oxadiazoles, thiazoles, thiadiazoles and benzothiazole.

The known 3β-(substituted phenyl)-2β-tropane carboxylic acid (tropane acid) (Carroll et al., *J. Med. Chem.* 35:1813-1817 (1992)) served as the starting material for the synthesis of 2β-substituted tetrazoles, oxazoles, oxadiazoles, thiazoles, thiadiazoles and benzothiazole as shown in FIG. 1.

The tropane acid was refluxed with N-acetyl and benzoic hydrazide in phosphorous oxychloride to obtain the corresponding 5-substituted 1,3,4-oxadiazoles (Afanasiadi et al., *Chem. Heterocyclic Compd.* 397-400 (1995)). N-benzoyl hydrazide amide obtained by the reaction of the acid chloride of tropane acid with N-benzoic hydrazide was cyclized with Lawesson's reagent (El-Barbary et al., *Acta Chimica Scandinavica* 597-601 (1980)) in refluxing THF to the 5-substituted 1,3,4-thiadiazoles. The N-phenylacyl carboxamide obtained from tropane acid and 2-aminoacetophenone was cyclized by refluxing the amide in phosphorous oxychloride to obtain the required 5-substituted oxazoles (Carroll et al., *Med. Chem. Res.* 3:468 (1993)). Cyclization of the same amide with Lawesson's reagent (El-Barbary et al., 1980) in refluxing THF gave the 5-substituted thiazoles respectively. The benzothiazole was obtained without the cyclization step by the reaction of acid chloride obtained from the appropriate tropane acid with 2-aminothiophenol.

Figure 2:
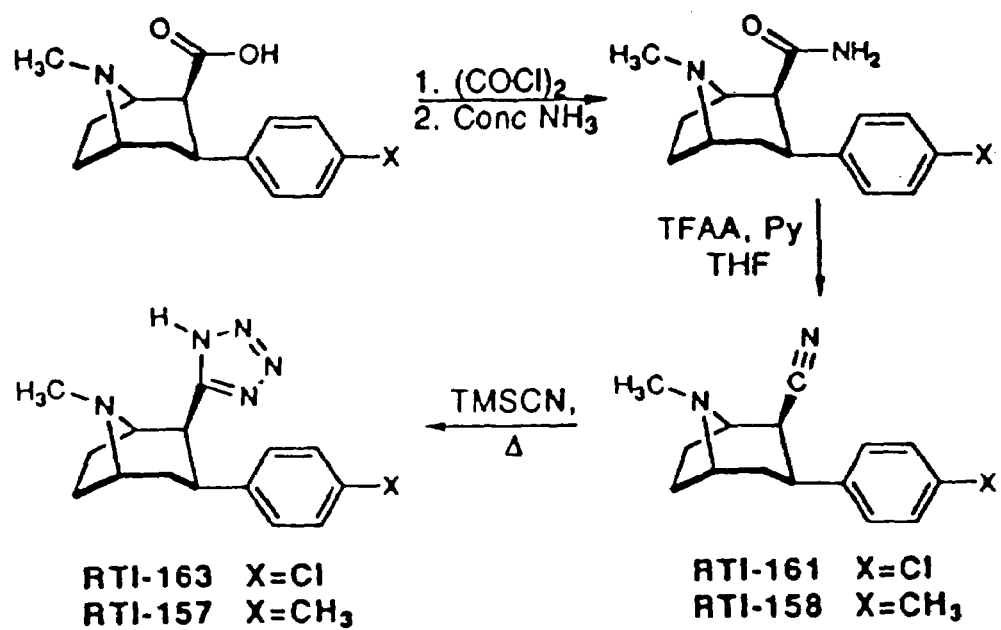
FIG. 2 depicts the scheme in which the carboxamide obtained from the tropane acid was treated to obtain nitrites and tetrazoles.

The previously reported carboxamide (Carroll et al., 1993) obtained from the tropane acid was dehydrated with trifluoroacetic acid and pyridine in THF to the nitriles (Campagna et al., *Tet. Letts.* 22:1813-1816 (1977)) as shown in FIG. 2. Cycloaddition of trimethylsilylazide to the nitrile afforded the corresponding tetrazoles (Saunders et al., *Med. Chem.* 33:1128-1138 (1990)).

Figure 3:
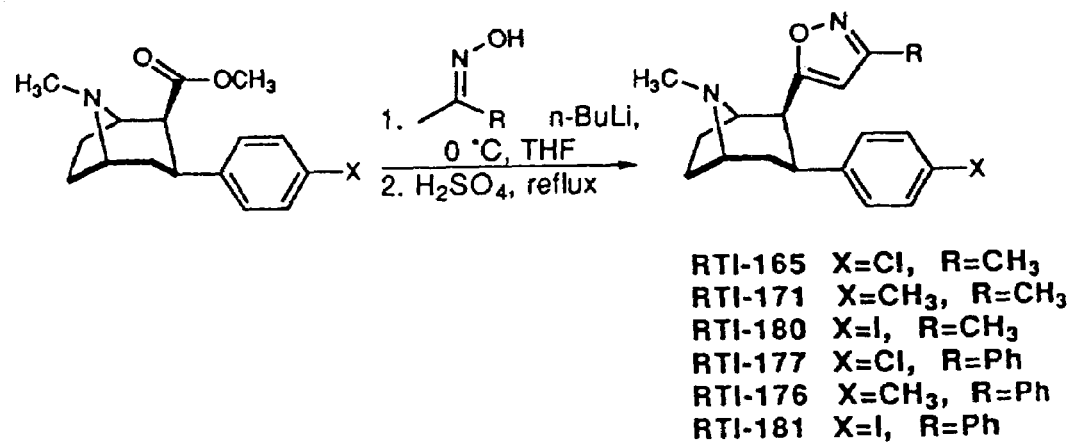
FIG. 3 depicts the scheme used to prepare 3-substituted isoxazoles.

FIG. 3 outlines the route used to prepare 3-substituted isoxazole. The known tropane compounds (Carroll et al., *J. Med. Chem.* 34:2719-2725 (1991)) were treated with dilithiated methyl or phenyl acetoneoximes, obtained by the treatment of acetone or acetophenoneoxime with n-BuLi at 0° C. The corresponding addition product was cyclized without isolation using sulfuric acid at reflux temperature to furnish the required isoxazoles (Saunders et al., 1990).

The therapeutic effects of the present cocaine analogs can be analyzed in various ways, many of which are well known to those of skill in the art. In particular, both in vitro and in vivo assay systems may be used for the screening of potential drugs which act as agonists or antagonists at cocaine receptors, or drugs which are effective to modulate neurotransmitter level or activity, in particular by binding to a transporter of that neurotransmitter.

The compounds of the invention may be prepared and labeled with any detectable moiety, in particular a radioactive element, and may then be introduced into a tissue or cellular sample. After the labeled material or its binding partner(s) has had an opportunity to react with sites within the sample, the location and concentration of binding of the compound may be examined by known techniques, which may vary with the nature of the label attached.

Illustrative in vitro assays for binding are described in Boja et al *Ann. NY Acad. Sci.* 654:282-291 (1992), which is incorporated herein by reference in its entirety. A particularly preferred in vitro assay involves the ability of a compound in question to displace the binding of a known labelled compound to binding sites in a tissue sample, isolated membranes or synaptosomes. Alternatively, the compounds may be analyzed by their ability to inhibit reuptake of a labelled neurotransmitter in a sample, in particular, in synaptosomes.

The compound or its binding partner(s) can also be labeled with any detectable moiety, but are preferably labelled with a radioactive element. The radioactive label can be detected by any of the currently available counting procedures, including the imaging procedures detailed in the disclosures of the parent applications. The preferred isotope may be selected from $^{3}H$, $^{11}C$, $^{14}C$, $^{11}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.c, As noted in the parent disclosures, the binding of the labelled compounds may be analyzed by various imaging techniques, including positron emission tomography (PET), single photon emission computed tomography (SPECT), autoradiogram, and the like. Such imaging techniques are useful for determining effective doses of new drug candidates. By performing in vivo competition studies, it is possible to use brain imaging studies to determine the oral doses of new drug candidates; which produce significant receptor occupancy in the brain. In vivo displacement studies which determine in vivo IC50's which in turn reflect doses that occupy receptors in vivo are described in Cline et al ((1992) *Synapse* 12:37-46). In addition to its uses in determining in vivo potency/occupancy, these same brain imaging methods can be used to determine rate of entry of compounds into the brain (Stathis et al (1995) *Psychopharmacology* 119:376-384) and duration of action (Volkow et al (1995) *Synapse* 19:206-211).

The binding of the compounds of the invention may be at any location where a receptor for a particular psychostimulant is present, and more specifically, any location where a dopamine or serotonin transporter is present. Such locations are in general any area comprising a part of the dopamine or serotonin pathway, in particular at synapses. Examples of locations known to be associated with dopamine transport include the cerebral cortex, hypothalamus, substantial nigra, nucleus accumbens, arcuate nucleus, anterior periventricular nuclei, median eminence and amygdala. Examples of locations known to be associated with serotonin include the stratum, cerebral cortex, hypothalamus, Raphe nuclei, preoptic area and suprachiasmatic nucleus.

By "psychostimulant" is meant any compounds whose abuse is dependent upon mesolimbic and mesocortical dopaminergic pathways. In particular, psychostimulant relates to cocaine. However, the compounds of the invention may also be used to treat abuse of compounds not traditionally classified as "psychostimulants," but which act at a dopamine or serotonin transporter. Such abused compounds include ethanol and nicotine.

For in vivo studies, the compounds of the invention may be prepared in pharmaceutical compositions, with a suitable carrier and at a strength effective for administration by various means to a patient experiencing an adverse medical condition associated with cocaine receptor binding or neurotransmitter release and reuptake, for the treatment thereof. The action of the compounds may be analyzed by the imaging methods noted above, and also by behavioral studies. In particular, the pharmaceutical effects of the compounds of the invention may be reflected in locomotor activity, including the induction of ipsilateral rotation, stereotyped sniffing and the "swim test", in schedule-controlled operant behavior (i.e., response for food or shock termination) or drug self-administration. In general, maximal behavioral effects are seen at near complete occupancy of transporter sites. Such protocols are described in Boja et al (1992), Balster et al *Drug and Alcohol Dependence* 29:145-

151 (1991), Cline et al *Pharm. Exp. Ther.* 260:1174-1179 (1992), and Cline et al *Behavioral Pharmacology* 3:113-116 (1992), which are hereby incorporated herein by reference in their entireties.

A variety of administrative techniques may be utilized, among them oral or parenteral techniques such as subcutaneous, intravenous, intraperitoneal, intracerebral and intracerebroventricular injections, catheterizations and the like. Average quantities of the compounds may vary in accordance with the binding properties of the compound (i.e., affinity, onset and duration of binding) and in particular should be based upon the recommendations and prescription of a qualified physician or veterinarian.

The compounds of the invention preferably have a long duration of action, which is important to facilitate dosing schedules. In rats, the present compounds have a 7-10 fold longer duration of action than cocaine (Fleckenstein et al, "Highly potent cocaine analogs cause long-lasting increases in locomotor activity," *Eur. J. Pharmacol.*, in press, which is incorporated herein by reference in its entirety). In addition, the present compounds also preferably have a slow rate of entry into the brain, which is important in decreasing the potential for abuse (Stathis et al, supra, which is incorporated herein by reference in its entirety). The present compounds enter the brain more slowly than cocaine.

The therapeutic compositions useful in practicing the therapeutic methods of this invention may include, in admixture, a pharmaceutically acceptable excipient (carrier) and one or more of the compounds of the invention, as described herein as an active ingredient.

The preparation of therapeutic compositions which contain such neuroactive compounds as active ingredients is well understood in the art. Such compositions may be prepared for oral adminstration, or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, and pH buffering agents which enhance the effectiveness of the active ingredient. The compounds of the invention can be formulated into the therapeutic composition as neutralized pharmaceutically acceptable salt forms.

The therapeutic compositions are conventionally administered orally, by unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, the presence of other agonists and antagonists in the subject's system, and degree of binding or inhibition of binding desired. Precise amounts of active ingredient required to be administered depend on the judgment of the practitioner and are peculiar to each individual. However, suitable dosages may range from about 0.01 to about 1000, preferably about 0.25 to about 500, and more preferably 10 to 50 milligrams of active ingredient per kilogram body weight of individual per day and depend on the route of administration. However, the exact dosage must be determined by factoring in rate of degradation in the stomach, absorption from the stomach, other medications administered, etc. Suitable regimes for administration and are also variable, but are typified by an initial administration followed by repeated doses at one or more hour intervals by a subsequent injection or other administration. Alternatively, continuous intravenous infusion sufficient to maintain appropriate concentrations in the blood are contemplated.

The compounds of the present invention may be administered for their activities as surrogate agonist medications for cocaine, nicotine, alcohol, amphetamine and other psychostimulant abuse. Because of their favorable binding characteristics to transporters of neurotransmitters, they may be used for inhibiting the uptake of dopamine, norepinephrine, serotonin and other monoamines. The compounds of the present invention may find use as antipsychotics, antidepressants, local anesthetics, anti-Parkinsonian agents, anti-obesity drugs, drugs useful in the treatment of bipolar disorder, eating disorders, obesity, attention deficit disorder, panic attacks and disorder, obsessive-compulsive disorder, sexual dysfunction, as anticholinergic agents and as sigma receptor drugs.

The compounds of the invention may also be useful in treating neurodegenerative disorders, in particular for treating Parkinson's Disease, but also may be useful in the treatment of cocaine, nicotine and alcohol addiction.

The preferred compounds of the present invention are derived from the series of compounds designated RTI-4229. The physical properties of some of these compounds are given in Table I.

TABLE I

Physical Properties of 2β-substituted Hetrocyclic Analogs of 3β-(4-Substituted-phenyl) Tropane and Cocaine

| code name | Compound | Molecular Formulae[a] | mp° C. | [α]$_D$ (c) MeOH | Yield % |
|---|---|---|---|---|---|
| RTI-188 | | $C_{22}H_{23}Cl_2N_3O$[e] | 160-162 | +84.59 (0.36) | 42 |
| RTI-195 | | $C_{23}H_{26}ClN_3O$[e] | 175-178 | +97.22 (0.25) | 40 |
| RTI-194 | | $C_{18}H_{24}ClN_3O$[d] | 146 (dec) | −43.05 (0.15) | 58 |
| RTI-200 | | $C_{22}H_{23}Cl_2N_3S$[e] | 165-170 | −42.81 (0.16) | 58 |
| RTI-199 | | $C_{23}H_{26}ClN_3S$[d] | 180-185 | −33.50 (0.20) | 58 |
| RTI-189 | | $C_{27}H_{29}ClN_2O_7$[b,e] | 126 (dec) | +101.43 (0.21) | 49 |
| RTI-178 | | $C_{28}H_{32}N_2O_7$[b,f] | 175-181 | −104.04 (0.60) | 72 |
| RTI-219 | | $C_{23}H_{24}ClN_2S$[f] | 228-230 | +27.43 (0.11) | 30 |
| RTI-202 | | $C_{21}H_{22}Cl_2N_2S$[e] | 140-150 (dec) | −172.49 (0.28) | 41 |

TABLE I-continued

Physical Properties of 2β-substituted Hetrocyclic Analogs of 3β-(4-Substituted-phenyl) Tropane and Cocaine

| code name Compound | Molecular Formulae[a] | mp° C. | [α]$_D$ (c) MeOH | Yield % |
|---|---|---|---|---|
| RTI-161 | $C_{15}H_{18}Cl_2N_2$[e] | >220 (dec) | −71.00 (0.50) | 77 |
| RTI-158 | $C_{16}H_{21}ClN_2$ | 270 (dec) | −76.40 (0.50) | 67 |
| RTI-163 | $C_{15}H_{18}ClN_5$[e] | 296-300 | −124.94 (0.39) | 33 |
| RTI-157 | $C_{16}H_{23}Cl_2N_5$[e] | >212 (dec) | −110.97 (0.16) | 88 |
| RTI-165 | $C_{18}H_{22}Cl_2N_2O$ | 235 (dec) | −102.89 (0.46) | 46 |
| RTI-171 | $C_{19}H_{25}ClN_2O$ | 277 | −107.28 (0.71) | 62 |
| RTI-180 | $C_{18}H_{22}ClN_2O$[c] | >235 (dec) | −94.57 (0.39) | 49 |
| RTI-177 | $C_{23}H_{24}Cl_2N_2O$[c] | 287 | −97.50 (0.28) | 50 |
| RTI-176 | $C_{24}H_{27}ClN_2O$ | 270-295 (dec) | −102.22 (0.68) | 77 |
| RTI-181 | $C_{23}H_{24}ClN_2O$[d] | >2679 (dec) | −91.11 (0.43) | 56 |
| RTI-184 | $C_{19}H_{23}ClN_2O_3$[d] | 117-121 | −53.60 (0.25) | 82 |
| RTI-185 | $C_{24}H_{25}ClN_2O_3$ | 205 | −56.71 (0.43) | 68 |

[a]HCl Salt;
[b]Tartrate Salt
[c]0.25 mol water;
[d]0.5 mol water;
[e]0.75 mol water;
[f]1 mol water.

Many of the preferred compounds of the invention fall within the broad class of compounds described by the formula:

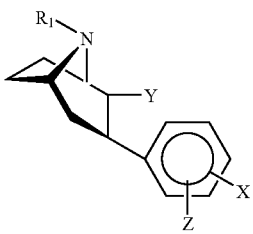

Wherein Y=$CH_2R_3$, $CO_2R_2$, $CONRR^1$

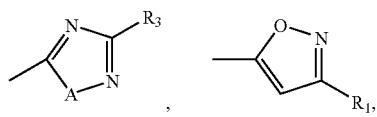

$R_1$=hydrogen, $C_{1-5}$ alkyl, $R_2$=hydrogen, $C_{1-6}$ alkyl, $C_{3-8}$ cycloalkyl, $C_{1-4}$ alkoxy, $C_{1-6}$alkynyl, halogen, amine, $CH_2C_6H_5$, $(CH_2)_2C_6H_5$, $(CH_2)_3C_6H_5$ or

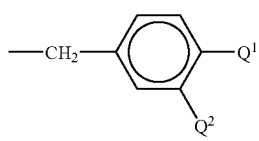

$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, $OCOC_{1-3}$ alkylaryl, A=S, O or N X=H, $C_{1-6}$ alkyl, $C_{3-8}$ cycloalkyl, $C_{1-4}$ alkoxy, $C_{1-6}$ alkynyl, halogen, amino, acylamido, $C_2H_5$, $CH_2CH_3CH_3$, $CH(CH_3)_2$, Z=H, I, Br, Cl, F, CN, $CF_3$, $NO_2$, $N_3$, $OR_1$, $CONH_2$, $CO_2R_1$, $C_{1-6}$ alkyl, $NR_4R_5$, $NHCOR_5$, $NHCO_2R_6$, and $Q^1$ and $Q^2$ may be the same or different and=H, $OCH_3$, or Cl, wherein $R_4$-$R_6$ are each $C_{1-6}$ alkyl, R and $R^1$ are independently H, $C_{1-6}$ alkyl, $C_{1-6}$ alkene, $C_{1-6}$ alkyne, phenyl, phenyl substituted with 1-3 of $C_{1-6}$ alkyl, alkene, alkyl or alkoxy, $C_{1-6}$ alkoxy, phenoxy, amine, amine substituted with 1-2 of $C_{1-6}$ alkyl, alkene, alkyne, alkoxy or phenyl or phenoxy or R and $R^1$ may combine to form heterocyclic structure including pyrrolidinyl, piperidinyl and morpholino moieties, unsubstituted or substituted with 1-2 $C_{1-6}$ alkyl, alkene, alkyne or alkoxy groups.

The present inventors have surprisingly found that certain of the RTI-4229 series of compounds are particularly potent pharmaceutical agents in accordance with the present invention.

Preferred compounds of the RTI-4229 series include the following: RTI-4229-31, 32, 51, 55, 83, 96, 97, 98, 101, 105, 108, 110, 111, 112, 116, 121, 122, 127, 132, 139, 140, 142, 145, 146, 147, 150, 153, 178, 188, 189, 190, 191, 193, 195, 199, 200, 203, 204, 205, 206, 219, 230, 239, 240, 241, 242, 251, 252, 274, 277, 278, 279, 280, 281, 282, 283, 286, 287, 296, 304, 305, 307, 309, 318, and 330. The chemical structures of these compounds, along with their $IC_{50}$ values for inhibition of radioligand binding are given below. DA is dopamine, 5-HT is 5-hydroxytryptamine (serotonin), and NE is norepinephrine, DA=[$^3$H]WIN 35,428; 5-HT=[$^3$H] paroxetine and $NE_N$=[$^3$H] nisofetine:

RTI-4229-31 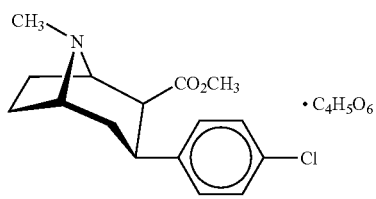
| | |
|---|---|
| DA | 1.12 ± 0.1 |
| 5-HT | 44.5 ± 1.34 |
| $NE_N$ | 37 ± 2.1 |
RTI-4229-32 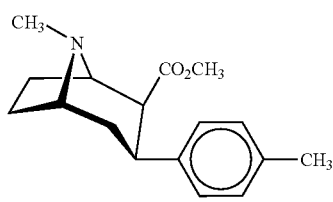
| | |
|---|---|
| DA | 1.71 ± 0.31 |
| 5-HT | 240 ± 27 |
| $NE_N$ | 60 ± 0.53 |
RTI-4229-51 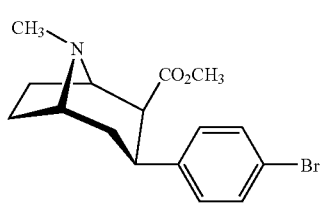
| | |
|---|---|
| DA | 1.69 ± 0.23 |
| 5-HT | 10.6 ± 0.24 |
| $NE_N$ | 37.4 ± 5.2 |
RTI-4229-55 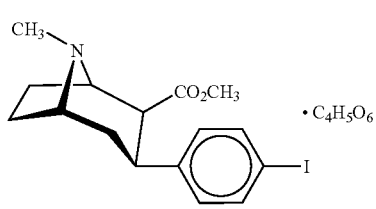
| | |
|---|---|
| DA | 1.26 ± 0.04 |
| 5-HT | 4.21 ± 0.34 |
| $NE_N$ | 36 ± 3 |
RTI-4229-83 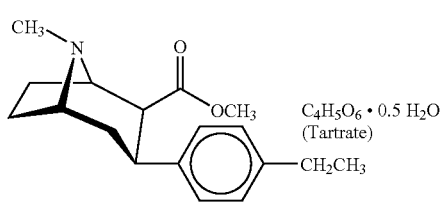
| | |
|---|---|
| DA | 55 ± 2 |
| 5-HT | 28.4 ± 3.83 |
| $NE_N$ | 4027.87 ± 380.70 |

-continued
RTI-4229-96 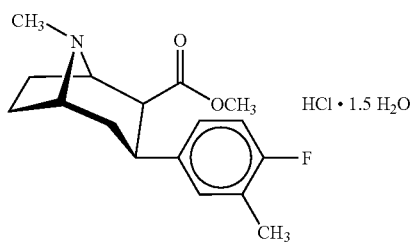 HCl · 1.5 H₂O
| | |
|---|---|
| DA | 2.95 ± 0.58 |
| 5-HT | 78 ± 2.8 |
| NE$_N$ | 520 ± 10.4 |
RTI-4229-97 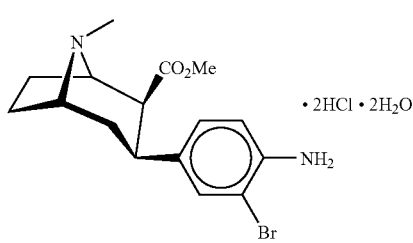 · 2HCl · 2H₂O
| | |
|---|---|
| DA | 3.91 ± 0.59 |
| 5-HT | 181 ± 14 |
| NE$_N$ | 282 ± 30 |
RTI-4229-98 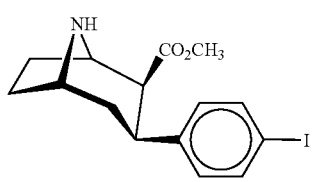
| | |
|---|---|
| DA | 0.89 ± 0.2 |
| 5-HT | 0.36 ± 0.047 |
| NE$_N$ | 10.97 ± 0.88 |
RTI-4229-101 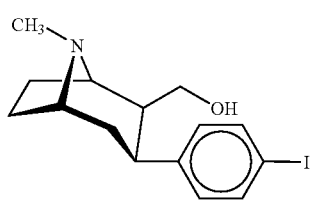
| | |
|---|---|
| DA | 2.2 ± 0.19 |
| 5-HT | 28 ± 3.2 |
| NE$_N$ | ± |
RTI-4229-105 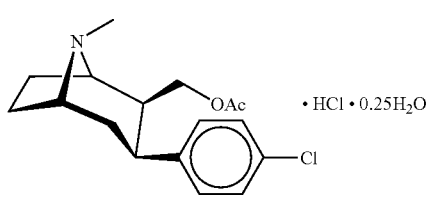 · HCl · 0.25H₂O
| | |
|---|---|
| DA | 1.60 ± 0.05 |
| 5-HT | 143 ± 25 |
| NE$_N$ | 127.2 ± 5.9 |

-continued
RTI-4229-108
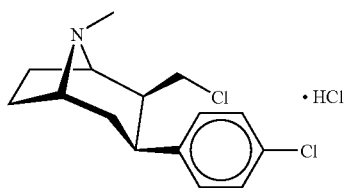
| | |
|---|---|
| DA | 2.64 ± 0.31 |
| 5-HT | 98 ± 8.7 |
| $NE_N$ | 129.3 ± 15 |
RTI-4229-110
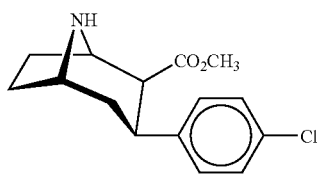
| | |
|---|---|
| DA | 0.62 ± 0.09 |
| 5-HT | 4.13 ± 0.62 |
| $NE_N$ | 5.45 ± 0.21 |
RTI-4229-111
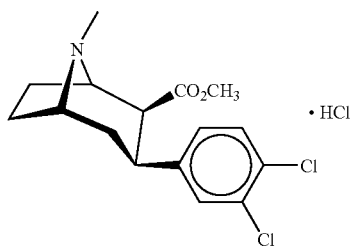
| | |
|---|---|
| DA | 0.79 ± 0.00 |
| 5-HT | 3.13 ± 0.36 |
| $NE_N$ | 17.90 ± 0.65 |
RTI-4229-112
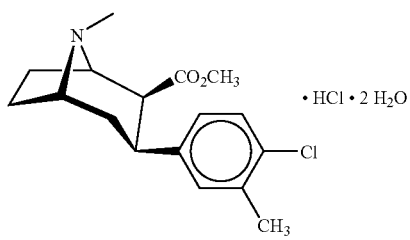
| | |
|---|---|
| DA | 0.82 ± 0.05 |
| 5-HT | 10.5 ± 0.41 |
| $NE_N$ | 36.2 ± 1.02 |
RTI-4229-116
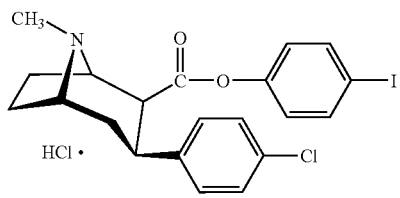
| | |
|---|---|
| DA | 33 ± 3.9 |
| 5-HT | 1,227 ± 176 |
| $NE_N$ | 967.55 ± 26.25 |

-continued
RTI-4229-121
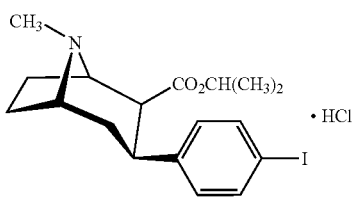
| | |
|---|---|
| DA | 0.43 ± 0.05 |
| 5-HT | 66.84 ± 6.53 |
| NE$_N$ | 285 ± 7.6 |
RTI-4229-122
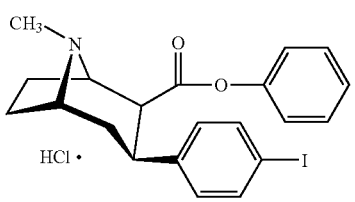
| | |
|---|---|
| DA | 1.50 ± 0.35 |
| 5-HT | 184.38 ± 21.91 |
| NE$_N$ | 3,791 ± 149 |
RTI-4229-127
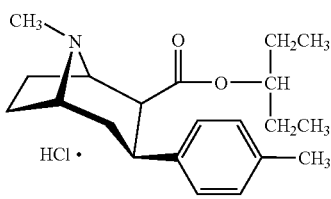
| | |
|---|---|
| DA | 19 ± 1 |
| 5-HT | 4,499 ± 557 |
| NE$_N$ | 3,444 ± 44 |
RTI-4229-132
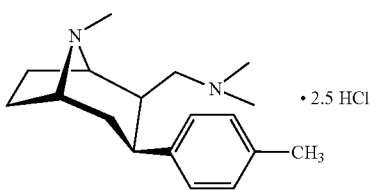
| | |
|---|---|
| DA | 3.48 ± 0.11 |
| 5-HT | 206 ± 16 |
| NE$_N$ | 137.3 ± 10.5 |
RTI-4229-139
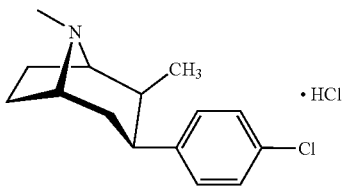
| | |
|---|---|
| DA | 1.67 ± 0.13 |
| 5-HT | 85 ± 9.3 |
| NE$_N$ | 56.9 ± 2.6 |

-continued
RTI-4229-140
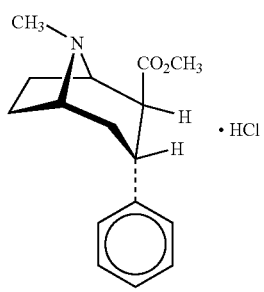
| | |
|---|---|
| DA | 101 ± 16 |
| 5-HT | 5.701 ± 721 |
| NE$_N$ | 2.076 ± 285 |
RTI-4229-142
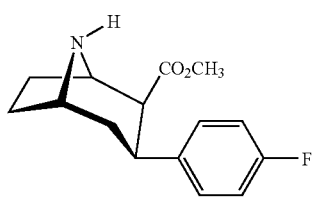
| | |
|---|---|
| DA | 4.39 ± 0.20 |
| 5-HT | 68.59 ± 2.02 |
| NE$_N$ | 18.78 ± 0.68 |
RTI-4229-145
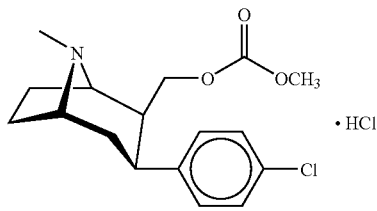
| | |
|---|---|
| DA | 9.60 ± 0.42 |
| 5-HT | 2.932 ± 181 |
| NE$_N$ | 1.476 ± 96 |
RTI-4229-146
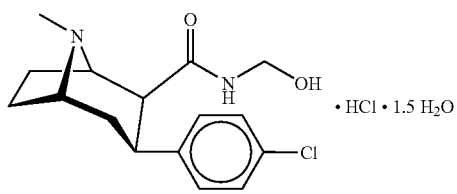
| | |
|---|---|
| DA | 2.05 ± 0.23 |
| 5-HT | 98 ± 10 |
| NE$_N$ | 144 ± 3 |
RTI-4229-147
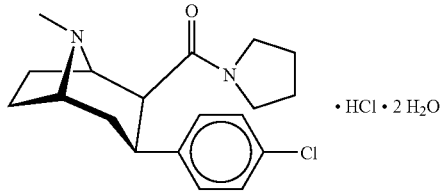
| | |
|---|---|
| DA | 1.38 ± 0.03 |
| 5-HT | 12,393.99 ± 1207.03 |
| NE$_N$ | 3,949 ± 72 |

-continued
RTI-4229-150 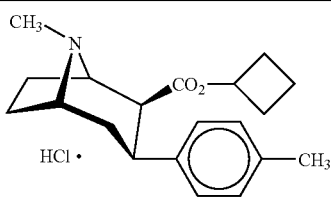
| | |
|---|---|
| DA | 3.74 ± 0.52 |
| 5-HT | 2,019 ± 133 |
| $NE_N$ | 4,738 ± 322 |
RTI-4229-153 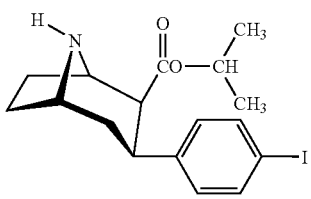
| | |
|---|---|
| DA | 1.06 ± 0.12 |
| 5-HT | 3.59 ± 0.27 |
| $NE_N$ | 132 ± 5 |
RTI-4229-173 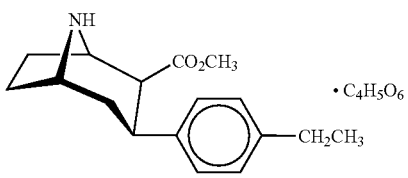
| | |
|---|---|
| DA | 49.9 ± 7.3 |
| 5-HT | 8.13 ± 0.30 |
| $NE_N$ | 122 ± 12 |
RTI-4229-178 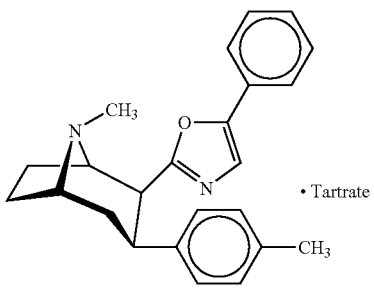
| | |
|---|---|
| DA | 35.4 ± 1.74 |
| 5-HT | 1,698.77 ± 166.68 |
| $NE_N$ | 677 ± 67.5 |
RTI-4229-188 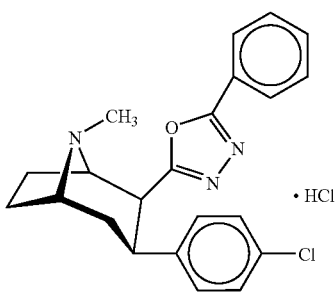
| | |
|---|---|
| DA | 12.56 ± 1.03 |
| 5-HT | 3,303.76 ± 195.85 |
| $NE_N$ | 929 ± 88.1 |

-continued
RTI-4229-189
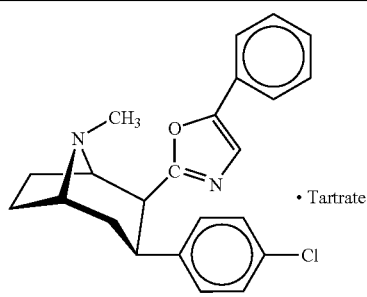
· Tartrate
| DA | 19.71 ± 1.96 |
| 5-HT | 1,116.18 ± 107,146 |
| NE$_N$ | 496 ± 42.1 |
RTI-4229-190
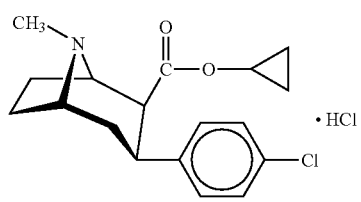
· HCl
| DA | 0.96 ± 0.10 |
| 5-HT | 168 ± 1.8 |
| NE$_N$ | 235 ± 8.39 |
RTI-4229-191
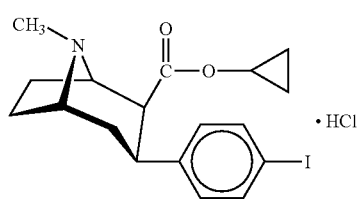
· HCl
| DA | 0.61 ± 0.08 |
| 5-HT | 15.5 ± 0.72 |
| NE$_N$ | 101.7 ± 10.5 |
RTI-4229-193
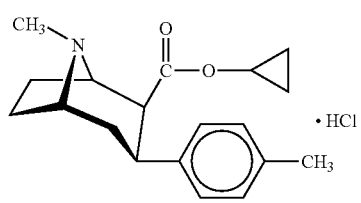
· HCl
| DA | 1.68 ± 0.14 |
| 5-HT | 1,068.38 ± 109.12 |
| NE$_N$ | 644 ± 27.7 |
RTI-4229-195
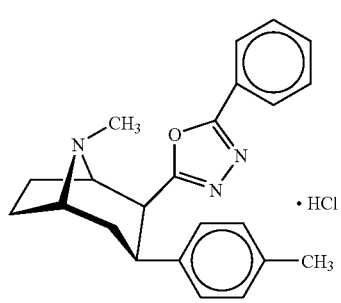
· HCl
| DA | 47.48 ± 4.76 |
| 5-HT | 22,310.9 ± 822.83 |
| NE$_N$ | 1,310 ± 36.7 |

-continued
RTI-4229-199
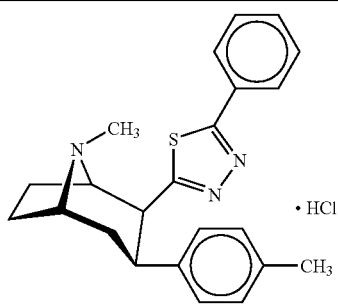
DA 35.88 ± 3.40
5-HT 51,459.7 ± 4,513.10
$NE_N$ 24,320.8 ± 3,822.61
RTI-4229-200
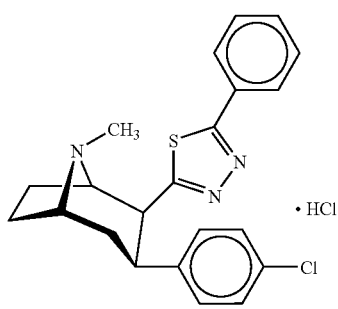
DA 15.29 ± 2.43
5-HT 18,416.5 ± 1,508.79
$NE_N$ 4,142.08 ± 66.07
RTI-4229-203
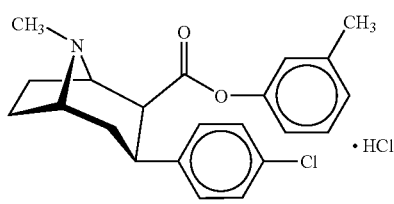
DA 9.37 ± 0.52
5-HT 2,153.39 ± 143.18
$NE_N$ 2,743.73 ± 140.92
RTI-4229-204
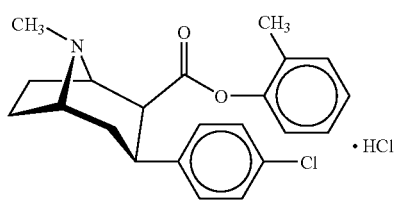
DA 3.91 ± 0.23
5-HT 3,772.17 ± 383.64
$NE_N$ 4,782.70 ± 487.10
RTI-4229-205
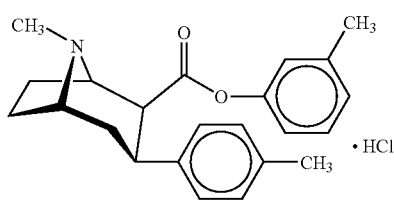
DA 8.19 ± 0.90
5-HT 5,237.30 ± 453.397
$NE_N$ 2,136.82 ± 208.52

-continued
RTI-4229-205
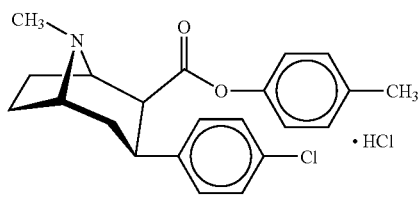
DA 27.38 ± 1.47
5-HT 1,203.39 ± 41.79
NE$_N$ 1,277.60 ± 117.68
RTI-4229-229
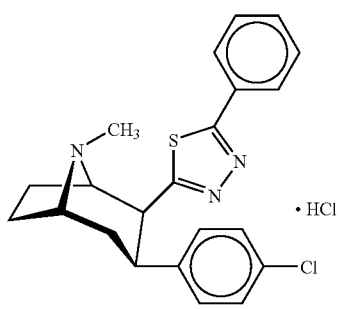
DA 5.71 ± 0.36
5-HT 10,341.5 ± 76.11
NE$_N$ 8,563 ± 824
RTI-4229-230
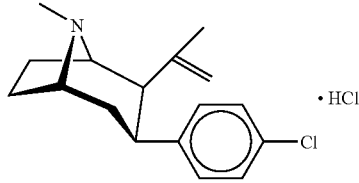
DA 1.28 ± 0.17
5-HT 57.41 ± 5.04
NE$_N$ 141 ± 16.1
RTI-4229-239
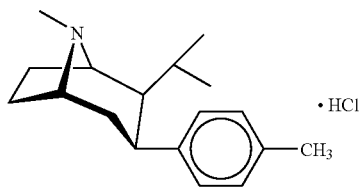
DA 0.61 ± 0.07
5-HT 114.3 ± 3.69
NE$_N$ 35.6 ± 2.57
RTI-4229-240
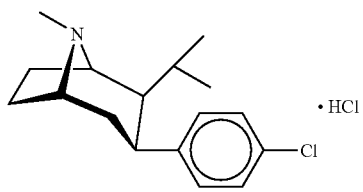
DA 1.36 ± 0.03
5-HT 36.4 ± 2.31
NE$_N$ 84.5 ± 3.09

-continued
RTI-4229-241
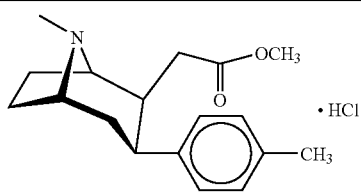
| | |
|---|---|
| DA | 1.02 ± 0.06 |
| 5-HT | 618.5 ± 28 |
| NE$_N$ | 124 ± 3.56 |
RTI-4229-242
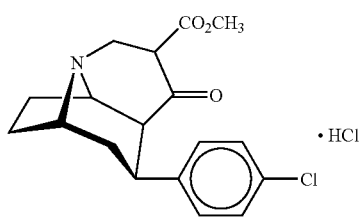
| | |
|---|---|
| DA | 7.67 ± 0.31 |
| 5-HT | 226.54 ± 27.37 |
| NE$_N$ | 510.1 ± 51.4 |
RTI-4229-251
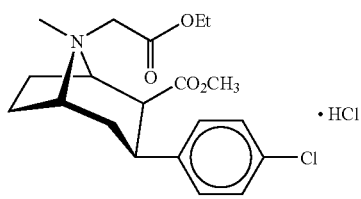
| | |
|---|---|
| DA | 1.93 ± 0.14 |
| 5-HT | 10.1 ± 1.1 |
| NE$_N$ | 114 ± 13.1 |
RTI-4229-252
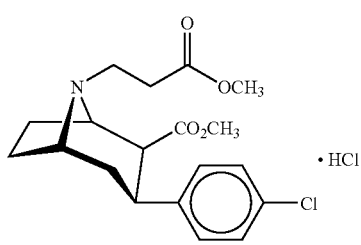
| | |
|---|---|
| DA | 2.56 ± 0.22 |
| 5-HT | 35.2 ± 2.45 |
| NE$_N$ | 124.6 ± 8.3 |
RTI-4229-274
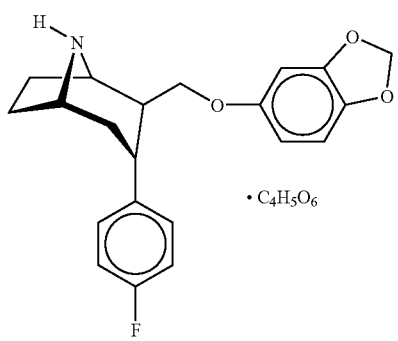
| | |
|---|---|
| DA | 3.96 ± 0.2 |
| 5-HT | 5.62 ± 0.2 |
| NE$_N$ | 14.4 ± 1.3 |

-continued
RTI-4229-277
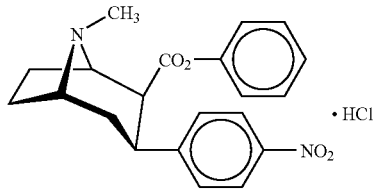
DA 5.94 ± 0.61
5-HT 2,909.71 ± 255.41
$NE_N$ 5,695.38 ± 214.72
RTI-4229-278
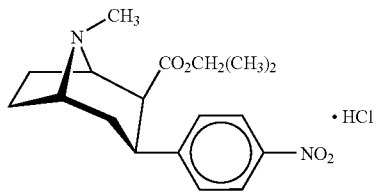
DA 8.14 ± 0.73
5-HT 2,146.50 ± 138.71
$NE_N$ 4,095.01 ± 413.45
RTI-4229-279
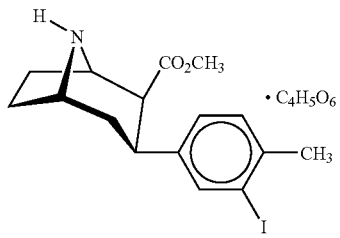
DA 5.98 ± 0.48
5-HT 1.06 ± 0.10
$NE_N$ 74.3 ± 3.8
RTI-4229-280
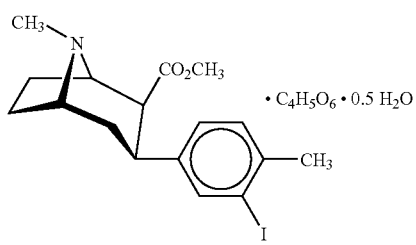
DA 3.12 ± 0.39
5-HT 6.81 ± 0.41
$NE_N$ 484.13 ± 51.8
RTI-4229-281
BIH-141-7
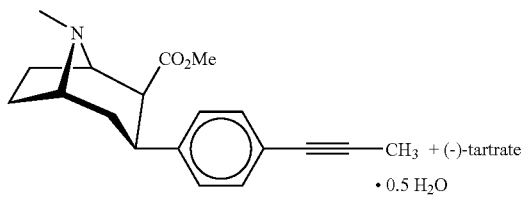
DA 2.37 ± 0.28
5-HT 15.69 ± 1.5
$NE_N$ 820.5 ± 45.8

-continued
RTI-4229-282
BIH-141-2
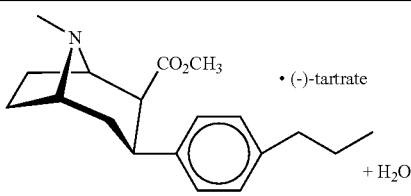
• (−)-tartrate
+ H₂O
| | |
|---|---|
| DA | 68.53 ± 7.08 |
| 5-HT | 70.38 ± 4.13 |
| NE$_N$ | 3921.58 ± 130 |
RTI-4229-283
BIH-141-12
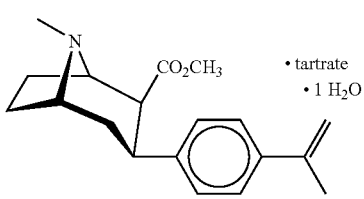
• tartrate
• 1 H$_2$O
| | |
|---|---|
| DA | 14.35 ± 0.3 |
| 5-HT | 3.13 ± 0.16 |
| NE$_N$ | 3125 ± 333 |
RTI-4229-286
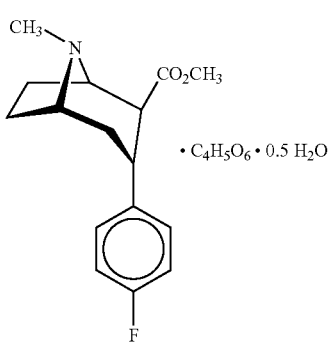
• C$_4$H$_5$O$_6$ • 0.5 H$_2$O
| | |
|---|---|
| DA | 20.7 ± 0.57 |
| 5-HT | 5062 ± 485 |
| NE$_N$ | 1231 ± 91 |
RTI-4229-287
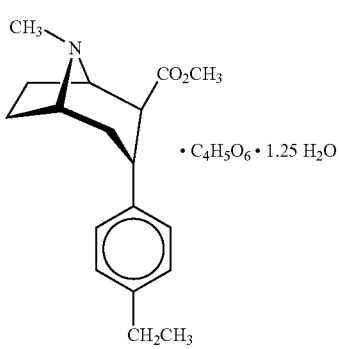
• C$_4$H$_5$O$_6$ • 1.25 H$_2$O
| | |
|---|---|
| DA | 325 ± 20 |
| 5-HT | 1686 ± 140 |
| NE$_N$ | 17,819 ± 440 |
RTI-4229-296
BIH-141-1
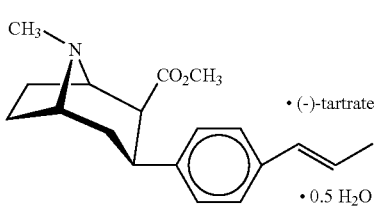
• (−)-tartrate
• 0.5 H$_2$O -continued
| | |
|---|---|
| DA | 5.29 ± 0.53 |
| 5-HT | 11.39 ± 0.28 |
| $NE_N$ | 1592.23 ± 93.4 |
RTI-4229-304
BIH-141-11
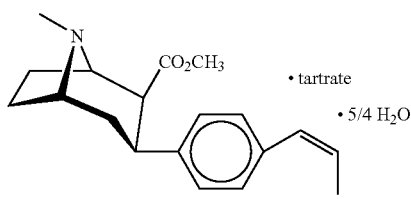
· tartrate
· 5/4 $H_2O$
| | |
|---|---|
| DA | 15.04 ± 1.2 |
| 5-HT | 7.09 ± 0.71 |
| $NE_N$ | 2799 ± 300 |
RTI-4229-305
BIH-141-18
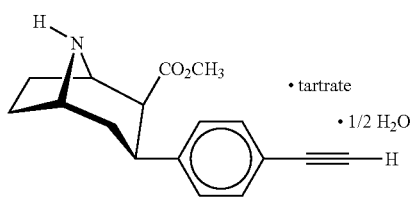
· tartrate
· 1/2 $H_2O$
| | |
|---|---|
| DA | 1.24 ± 0.11 |
| 5-HT | 1.59 ± 0.2 |
| $NE_N$ | 21.8 ± 1.0 |
RTI-4229-307
BIH-141-15
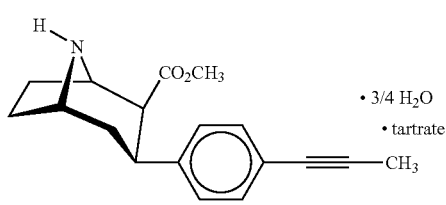
· 3/4 $H_2O$
· tartrate
| | |
|---|---|
| DA | 8.11 ± 0.67 |
| 5-HT | 3.16 ± 0.33 |
| $NE_N$ | 115.8 ± 5.1 |
RTI-4229-309
BIH-141-17
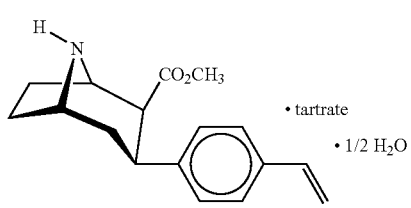
· tartrate
· 1/2 $H_2O$
| | |
|---|---|
| DA | 1.73 ± 0.05 |
| 5-HT | 2.25 ± 0.17 |
| $NE_N$ | 14.9 ± 1.16 |
RTI-4229-318
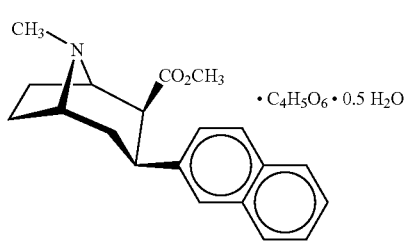
· $C_4H_5O_6$ · 0.5 $H_2O$
| | |
|---|---|
| DA | 0.51 ± 0.03 |
| 5-HT | 0.80 ± 0.06 |
| $NE_N$ | 21.1 ± 1.0 |

-continued
| | | |
|---|---|---|
| RTI-4229-330 | 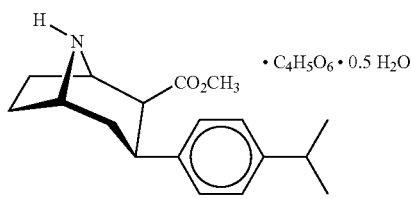 | |
| DA | 310.2 ± 21 | |
| 5-HT | 15.1 ± 0.97 | |
| NE$_N$ | ± | |
Particularly preferred compounds include RTI-4229-77, 87, 113, 114, 117, 119, 120, 124, 125, 126, 130, 141, 143, 144, 151, 152, 154, 165, 171, 173, 176, 177, 180, 181, 194, 202, 295, 298, 319, 334, 335, 336, 337, 338, 345, 346, 347, 348, 352 and 353. The chemical structures of these compounds are given below:
| | | |
|---|---|---|
| RTI-4229-77 | 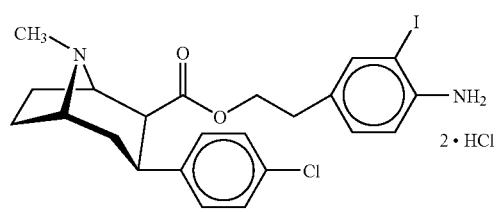 | |
| DA | 2.51 ± 0.25 | |
| 5-HT | ± | |
| NE$_N$ | 2.246.66 ± 238.99 | |
| RTI-4229-87 | 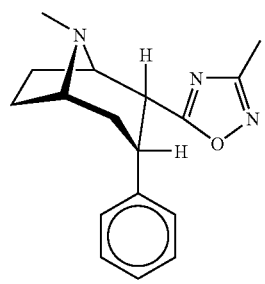 | |
| DA | 204 ± 29 | |
| 5-HT | 29.391 ± 2.324 | |
| NE$_N$ | 35.762 ± 6.245 | |
| RTI-4229-113 | 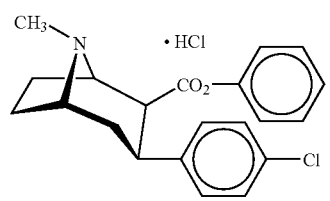 | |
| DA | 1.98 ± 0.05 | |
| 5-HT | 2.336 ± 176 | |
| NE$_N$ | 2.955 ± 223 | |

-continued
RTI-4229-114
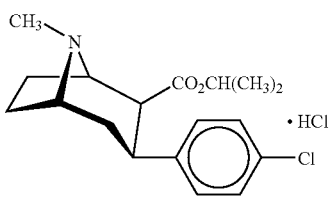
| | |
|---|---|
| DA | 1.40 ± 0.13 |
| 5-HT | 1.404 ± 7.1 |
| $NE_N$ | 776 ± 21 |
RTI-4229-117
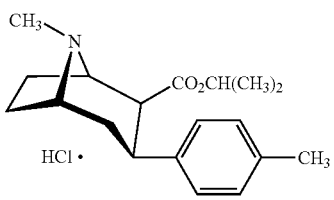
| | |
|---|---|
| DA | 6.45 ± 0.85 |
| 5-HT | 6.090 ± 468 |
| $NE_N$ | 1.926 ± 36 |
RTI-4229-119
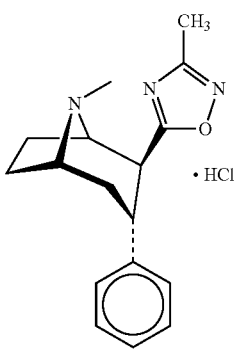
| | |
|---|---|
| DA | 167 ± 13 |
| 5-HT | 40.615 ± 9.416 |
| $NE_N$ | 6.965 ± 635 |
RTI-4229-120
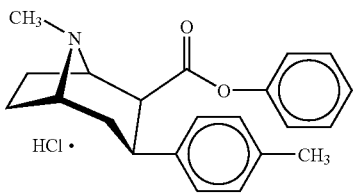
| | |
|---|---|
| DA | 3.26 ± 0.06 |
| 5-HT | 24,471 ± 1.515 |
| $NE_N$ | 5,833 ± 373 |
RTI-4229-124
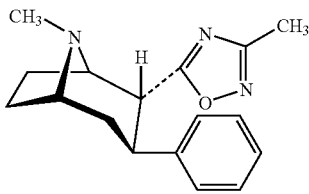
| | |
|---|---|
| DA | 1,028 ± 65 |
| 5-HT | 33.085 ± 5.434 |
| $NE_N$ | 70.993 ± 3.563 |

-continued
RTI-4229-125 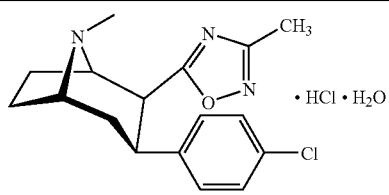
DA 4.05 ± 0.57
5-HT 2,584 ± 799
NE$_N$ 363 ± 36
RTI-4229-126 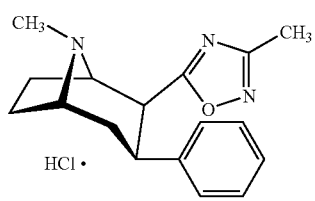
DA 100 ± 6.3
5-HT 3,824 ± 418
NE$_N$ 7,876 ± 551
RTI-4229-130 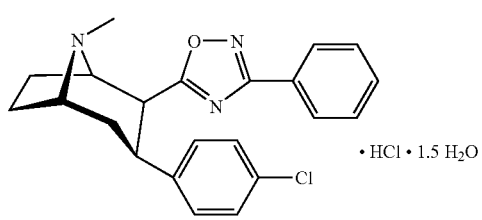
DA 1.62 ± 0.02
5-HT 195 ± 4.6
NE$_N$ 245 ± 13
RTI-4229-141 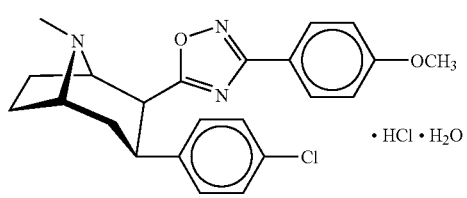
DA 1.81 ± 0.19
5-HT 337 ± 43
NE$_N$ 835 ± 7.5
RTI-4229-143 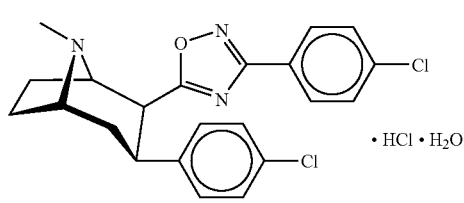
DA 4.1 ± 0.22
5-HT 404 ± 56
NE$_N$ 4,069 ± 177
RTI-4229-144 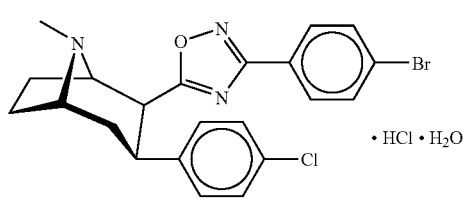

| | |
|---|---|
| DA | 3.44 ± 0.38 |
| 5-HT | 106 ± 10 |
| NE$_N$ | 1,825 ± 166 |
RTI-4229-151
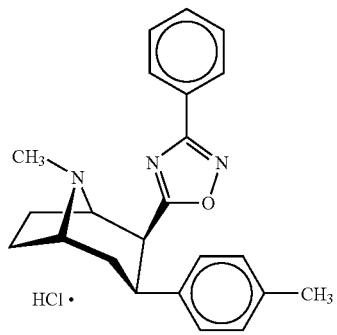
| | |
|---|---|
| DA | 2.33 ± 0.26 |
| 5-HT | 1,074 ± 125 |
| NE$_N$ | 60 ± 2 |
RTI-4229-152
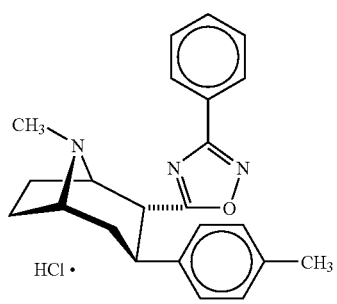
| | |
|---|---|
| DA | 494 ± 37 |
| 5-HT | 1,995 ± 109 |
| NE$_N$ | 22,689 ± 1,957 |
RTI-4229-154
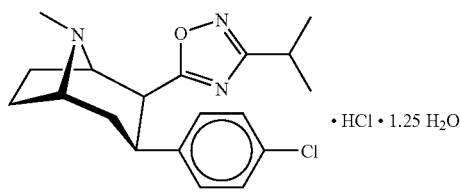
| | |
|---|---|
| DA | 6.0 ± 0.55 |
| 5-HT | 3.460 ± 245 |
| NE$_N$ | 135 ± 13 |
RTI-4229-165
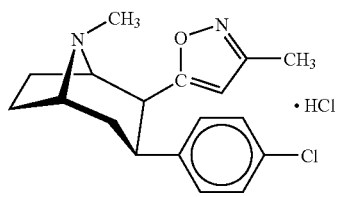
| | |
|---|---|
| DA | 0.59 ± 0.04 |
| 5-HT | 572 ± 58 |
| NE$_N$ | 131 ± 12 |

RTI-4229-171 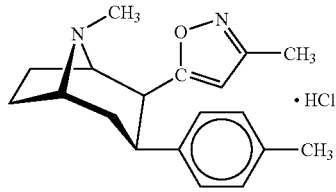
| | |
|---|---|
| DA | 0.93 ± 0.09 |
| 5-HT | 3,818.25 ± 346.14 |
| NE$_N$ | 254 ± 31 |
RTI-4229-176 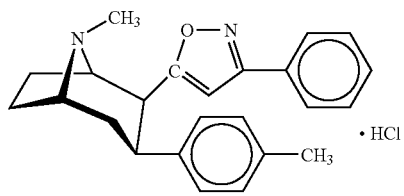
| | |
|---|---|
| DA | 1.58 ± 0.02 |
| 5-HT | 5.109.72 ± 187.101 |
| NE$_N$ | 398 ± 17.6 |
RTI-4229-177 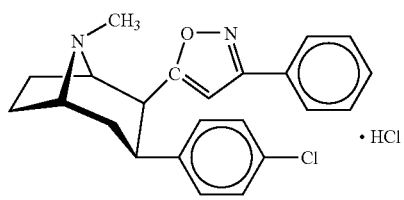
| | |
|---|---|
| DA | 1.28 ± 0.18 |
| 5-HT | 2,418.21 ± 135.68 |
| NE$_N$ | 504 ± 29 |
RTI-4229-180 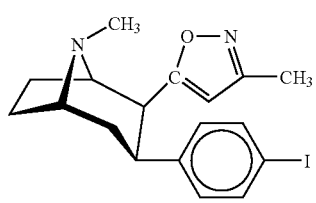
| | |
|---|---|
| DA | 0.73 ± 0.04 |
| 5-HT | 36.35 ± 4.99 |
| NE$_N$ | 67.9 ± 5.25 |
RTI-4229-181 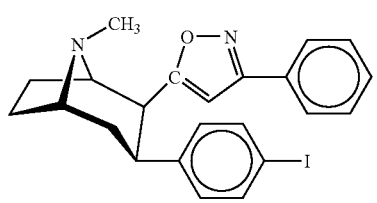
| | |
|---|---|
| DA | 2.57 ± 0.14 |
| 5-HT | 100 ± 9.0 |
| NE$_N$ | 868 ± 95 |

-continued
RTI-4229-194
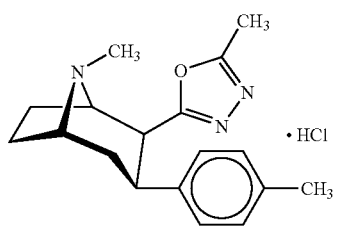
· HCl
| DA | 4.45 ± 0.12 |
| 5-HT | 4,884.47 ± 155.42 |
| $NE_N$ | 253 ± 18.9 |
RTI-4229-202
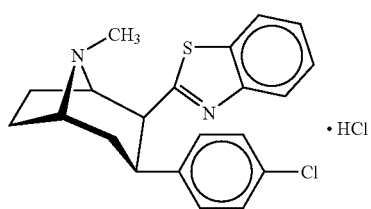
· HCl
| DA | 1.37 ± 0.14 |
| 5-HT | 1,118.85 ± 120.00 |
| $NE_N$ | 402.8 ± 29.5 |
RTI-4229-222
BIH-141-14
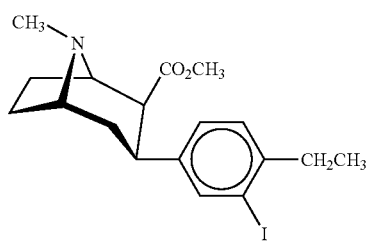
| DA | 21.31 ± 0.87 |
| 5-HT | 2.96 ± 0.04 |
| $NE_N$ | 1349 ± 105 |
RTI-4229-298
BIH-141-4
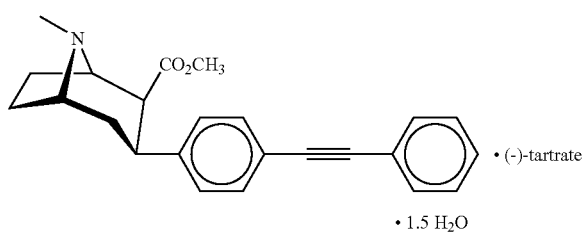
· (−)-tartrate
· 1.5 $H_2O$
| DA | 3.7 ± 0.16 |
| 5-HT | 46.8 ± 5.8 |
| $NE_N$ | 346.6 ± 25 |
RTI-4229-319
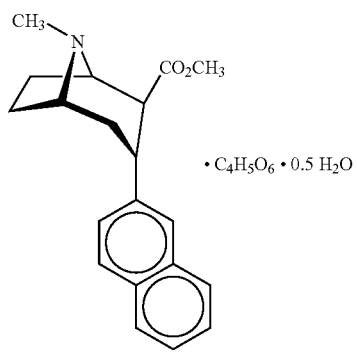
· $C_4H_5O_6$ · 0.5 $H_2O$ -continued
| | |
|---|---|
| DA | 1.1 ± 0.09 |
| 5-HT | 11.4 ± 1.3 |
| NE$_N$ | 70.2 ± 6.28 |
RTI-4229-334
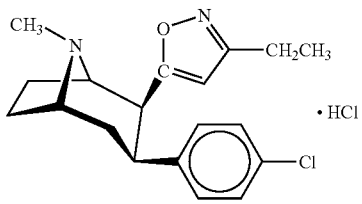
| | |
|---|---|
| DA | 0.50 ± 0.03 |
| 5-HT | 3088 ± 153 |
| NE$_N$ | 120 ± 10.4 |
RTI-4229-335
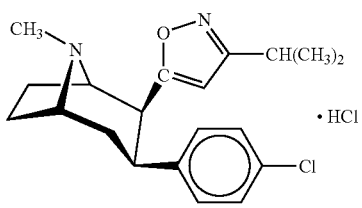
| | |
|---|---|
| DA | 1.19 ± 0.12 |
| 5-HT | 2318 ± 153 |
| NE$_N$ | 954 ± 97.3 |
RTI-4229-336
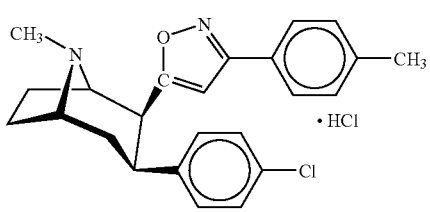
| | |
|---|---|
| DA | 409 ± 0.44 |
| 5-HT | 5741 ± 421 |
| NE$_N$ | 1714 ± 38.5 |
RTI-4229-337
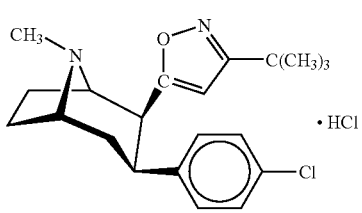
| | |
|---|---|
| DA | 7.31 ± 0.61 |
| 5-HT | 36,842 ± 3016 |
| NE$_N$ | 8321 ± 703 |
RTI-4229-338
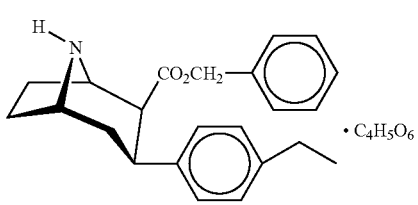
| | |
|---|---|
| DA | 1104.2 ± 54.6 |
| 5-HT | 7.41 ± 0.55 |
| NE$_N$ | 3366 ± 584 |

-continued
| | | |
|---|---|---|
| RTI-4229-345 | 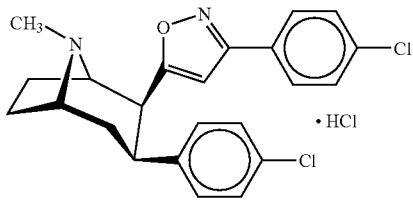 | |
| DA | 6.42 ± 0.46 | |
| 5-HT | >76,000 ± | |
| $NE_N$ | 5290.4 ± 448.99 | |
| RTI-4229-346 | 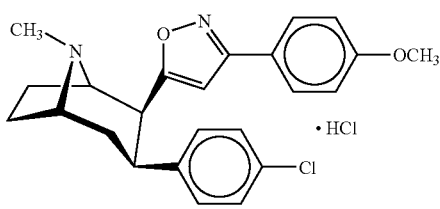 | |
| DA | 1.57 ± 0.10 | |
| 5-HT | 5880.4 ± 179 | |
| $NE_N$ | 762.01 ± 37.8 | |
| RTI-4229-347 | 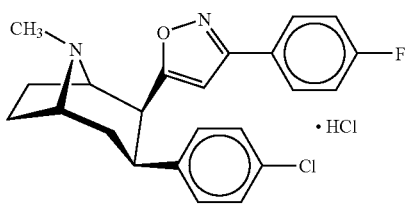 | |
| DA | 1.85 ± 0.09 | |
| 5-HT | 7256.95 ± 210 | |
| $NE_N$ | 918.4 ± 108.34 | |
| RTI-4229-348 | 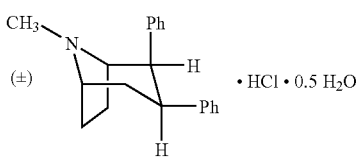 | |
| DA | 28.2 ± 1.9 | |
| 5-HT | 34,674 ± 3,954 | |
| $NE_N$ | 2667.2 ± 6267.3 | |
| RTI-4229-352 | 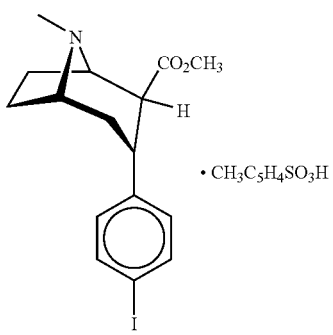 | |
| DA | 2.86 ± 0.21 | |
| 5-HT | 64.9 ± 1.97 | |
| $NE_N$ | 52.4 ± 4.9 | |

RTI-4229-353

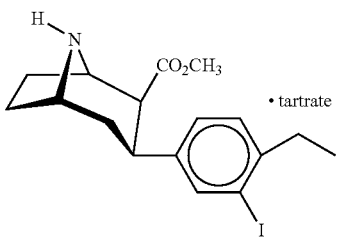

| | |
|---|---|
| DA | 330.54 ± 17.12 |
| 5-HT | 0.69 ± 0.07 |
| $NE_N$ | 148.4 ± 9.15 |

It should be noted that compound RTI-353 is a highly potent compound at the serotonin site, and is selective relative to the dopamine and norepinephrine sites. This compound is particularly useful as an antidepressant, and as an imaging agent for serotonin transporters.

Having generally described this invention, a further understanding can be obtained by reference to certain specific examples which are provided herein for purposes of illustration only and are not intended to be limiting unless otherwise specified.

EXAMPLES

All certified grade reagents or solvents were purchased from Aldrich Chemical Co. or Fluka Chemical Co. All reagents were normally used without further purification. When anhydrous conditions were required, solvents were distilled and dried by standard techniques immediately prior to use.

All air and moisture sensitive reactions were conducted under a prepurified nitrogen atmosphere in flame-dried glassware, previously dried at 150° C. Anhydrous solvents were transferred using conventional syringe or steel canula techniques under an inert atmosphere. Removal of solvents in vacuo was done on a Buchi rotavapor rotary evaporator operated at water aspirator pressure.

$^1$H NMR and $^{13}$C NMR spectra were recorded at 250 Mhz on a Bruker AM250 spectrometer. Optical rotations were recorded on at the Sodium D line on a Rudolph Research Autopol III polarimeter (1 dm cell). Melting point was recorded on a Uni-melt Thomas Hoover capillary melting point apparatus in open capillary tubes and were uncorrected. Elemental analysis were performed by Atlantic Microlab, Inc., Norcross, Ga.

Reaction products were purified by flash column chromatography using silica gel (mesh size 230-400) purchased from VWR Scientific. Thin layer chromatography (TLC) was performed on Whatman 254 nm fluorescent silica gel 60A (1×3 inches, 250 [μL thickness]) precoated TLC plates using the solvent systems indicated. Developed chromatograms were evaluated under 254 nm UV light or with iodine.

Example 1

General Procedure For the Preparation of Amides

To a solution of 1 mmol of 3β-(4-Chlorophenyl)-tropane-2β-carboxylic acid or3β-(4-Methylphenyl)-tropane-2β-carboxylic acid in 5 ml of methylene chloride was added dropwise with stirring under nitrogen 2.0 eq oxalyl chloride (2 M solution in methylene chloride). The resulting solution was stirred at room temperature for an hour after evolution of gas has ceased. The solvent was removed in vacuo at room temperature and then at high vacuum to remove residual traces of oxalyl chloride. The resulting residue of acid chloride was suspended in 5 ml methylene chloride under nitrogen at 0° C., and 2.0 eq of the amine hydrochloride containing 4.0 eq of triethylamine, or 2.5 eq of the amine free base was added. The mixture was stirred at room temperature overnight. Aqueous 3N NaOH (5 ml) was added to basify the reaction mixture, the organic layer was separated and the aqueous layer extracted with 3×10 ml chloroform. The combined organic layers were dried ($Na_2SO_4$), filtered and the solvent removed in vacuo to give crude product. The crude was purified by flash column chromatography or crystallization.

Example 2

3β-(4-Chlorophenyl)-2β-(5-phenyl-1,3,4-oxadiazol-2-yl)-tropane Hydrochloride (RTI-188)

To a solution of 0.59 g (2 mmol) of 3β-(4-Chlorophenyl)-tropane-2β-carboxylic acid (chloro acid) in 2 ml Of $POCl_3$ was added 0.31 g (2.2 mmol) of N-benzoic hydrazide and refluxed under nitrogen for 2 hours. The reaction mixture was cooled, poured into ice and rendered basic to pH 7-8 using concentrated $NH_4OH$. To the ice cold aqueous layer was added 10 ml brine and extracted thrice with 10 ml methylene chloride. The organic layers were combined dried ($NaSO_4$), filtered, and the solvent removed in vacuo to give 0.9 g of crude residue. Purification of the residue by flash column chromatography [50% (ether/triethylamine 9:1) in hexane] gave 0.33 g (42%) of pure oxadiazole (RTI-188) which was recrystallized from ether/petroleum ether: $^1$H NMR ($CDCl_3$) 1.81 (m, 3H), 2.18 (s, 3H), 2.26 (m, 2H), 2.66 (m, 1H), 3.33 (m, 2H), 3.51 (m, 2H), 7.16 (m, 4H) 7.45 (m, 3H), 7.86 (m, 2H); IR ($CHCl_3$) 2950, 1550, 1490, 1450, 1340, 1090 cm$^{-1}$; $[\alpha]_D$ -106.25° (c=0.08, $CHCl_3$).

The oxadiazole was converted into hydrochloride salt: $^1$H NMR (MeOD) 2.08 (m, 1H), 2.57 (m, 5H), 3.0 (s, 3H), 4.01 (m, 2H), 4.15 (m, 1H), 4.39 (m, 1H), 7.24 (m, 4H), 7.52 (m, 5H): mp 160-162° C.; Anal calcd. for $C_{22}H_{23}Cl_2N_3O \cdot 0.75H_2O$; C, 61.47; H, 5.74; N, 9.78; Cl, 16.50. Found: C, 61.47; H, 5.73; N, 9.76; Cl, 16.56; $[\alpha]_D$+ 84.59° (c, 0.36; $CH_3OH$).

Further elution gave as a second fraction 0.1 g (13%) of white solid which was characterized to be 3β-(4-Chlorophenyl)-2α-(5-phenyl-1,3,4-oxadiazol-2-yl)-tropane: $^1$H NMR ($CDCl_3$) 1.76 (m, 3H), 2.06 (s, 3H), 2.45 (s, 3H), 3.36 (m, 2H), 3.51 (m, 1H), 3.65 (m, 1H), 7.21 (m, 4H), 7.47 (m, 3H) 7.91 (m, 2H); mp 170-171° C.; Anal calcd. for $C_{22}H_{22}ClN_3O$; C, 69.55; H, 5.84; N, 11.06; Cl, 9.33. Found: C, 69.49; H, 5.85; N, 11.01; Cl, 9.41; $[\alpha]_D$+33.060 (c, 0.18; $CHCl_3$).

Example 3

3β-(4-Methylphenyl)-2β-(5-phenyl-1,3,4-oxadiazol-2-yl)-tropane Hydrochloride (RTI-195)

Reaction of 0.65 g (2.5 mmol) of 3β-(4-Methylphenyl)-tropane-2β-carboxylic acid (Methyl acid) as described above for RTI-188 gave after work-up and purification by flash column chromatography [(50% (ether/triethylamine 9:1) in hexane] 0.36 g (40%) of pure oxadiazole (RTI-195) which was recrystallized from ether/petroleum ether: $^1$H NMR (CDCl$_3$) 1.83 (m, 3H), 2.18 (s, 3H), 2.21 (s, 3H), 2.3 (m, 2H), 2.67 (m, 1H), 3.33 (m, 1H), 3.41 (m, 1H), 3.53 (m, 1H), 3.61 (m, 1H) 7.0 (m, 2 H). 7.13 (m, 2H), 7.44 (m, 3H), 7.86 (m, 2H); IR (CHCL$_3$) 2990, 1545, 1505, 1440, 1350. cm$^{-1}$; $[\alpha]_D$-163.92° (c, 0.2; CHCl$_3$).

The oxadiazole was converted into hydrochloride salt: $^1$H NMR (MeOD) 2.05 (m, 1H), 2.21 (s, 3H), 2.51 (m, 5H), 2.99 (s, 3 H), 3.86 (m, 1H), 3.95 (m, 1H), 4.14 (m, 1H), 4.35 (m, 1H), 7.02 (m, 4H) 7.53 (m, 5H); mp 175-178° C.; Anal calcd. for $C_{23}H_{26}ClN_3O.0.75H_2O$; C, 67.47; H, 6.77; N, 10.26; Cl, 8.66; found: C, 67.58; H, 6.79; N, 10.34; Cl, 8.78; $[\alpha]_D$+97.22° (c, 0.25; $CH_3OH$).

Further elution gave as a second fraction 0.18 g (20%) of solid which was characterized to be 3β-(4-Methylphenyl)-2α-(5-phenyl-1,3,4-oxadiazol-2-yl)-tropane which was recrystallized from ether/petroleum ether: $^1$H NMR (CDCl$_3$) 1.77 (m, 2H), 2.0 (m, 4H), 2.25 (s, 3H), 2.47 (s, 3H), 3.33 (m, 2H), 3.51 (m, 1H), 3.69 (d of d, J=y 2.6, 12 Hz, 1H), 6.91 (m, 2H) 7.03 (m, 2H). 7.45 (m, 2H), 7.45 (m, 3H), 7.89 (m, 2H); IR (CHCL$_3$) 3020, 1540, 1510, 1415, 1250, 1215. cm$_{-1}$; Anal clacd. for $C_{23}H_{25}N_3O$; C, 76.85; H, 7.01; N, 11.69. Found: C, 76.60; H, 7.12; N, 11.55; $[\alpha]_D$+40.73° (c, 0.28; CHCl$_3$).

Example 4

3β-(4-Methylphenyl)-2β-(5-methyl-1,3,4-oxadiazol-2-yl)-tropane Hydrochloride (RTI-194)

Reaction of 0.65 g (2.5 mmol) of methyl acid as described above for RTI-195 using 0.21 g (2.75 mmol) of N-acetic hydrazide gave after work-up and Purification by flash column chromatography [(75% (ether/triethylamine 9:1) in hexane] 0.29 g (39%) of pure oxadiazole (RTI-194) which was recrystallized from ether/petroleum ether: $^1$H NMR (CDCl$_3$) 1.75 (m, 3H), 2.18 (s, 3H), 2.22 (s, 3H), 2.25 (m, 2H), 2.35 (s, 3H), 2.56 (m, 1H), 3.24 (m, 1H), 3.4 (m, 2H), 3.47 (m, 1H) 7.0 (m, 4H); $^{13}$C NMR (CDCl$_3$) 11.06, 20.9, 25.08, 26.32, 34.11, 34.6, 41.83, 45.73, 61.97, 66.21, 127.11, 128.85, 135.85, 138.19, 162.5, 167.44; IR (CHCL$_3$) 2950, 1590, 1510, 1450, 1350, 1215 cm$^{-1}$; $[\alpha]_D$-108.47° (c, 0.14; CHCl$_3$).

The-oxadiazole was converted into hydrochloride salt: $^1$H NMR (MeOD) 1.99 (m, 1H), 2.23 (s, 3H), 2.27 (s, 3H), 2.47 (m, 5H), 2.94 (s, 3H), 3.72 (m, 1H), 3.79 (m, 1H), 4.10 (m, 1H), 4.23 (m, 1H), 7.05 (m, 4H); mp 146° C. (dec); Anal clacd. for $C_{18}H_{24}ClN_3O.0.5H_2O$; C, 63.06; H, 7.35; N, 12.26; Cl, 10.34. found: C, 63.21; H, 7.40; N, 12.07; Cl, 10.27; $[\alpha]_D$-43.05° (c, 0.15; $CH_3OH$).

Example 5

3β-(4-Chlorophenyl)-2β-(5-phenyl-1,3,4-thiadiazol-2-yl)-tropane Hydrochloride (RTI-200)

Reaction of 0.59 g (2 mmol) of 3β-(4-Chlorophenyl) tropane-2β-carboxylic acid as described above for the preparation of amides gave after purification of the crude by crystallizing from ethyl acetate/ether 0.52 g (66%) of pure N-[3β-(4-Chlorophenyl)-tropane-2β-carboxylic]-N'-benzoylhydrazide: $^1$H NMR (CDCl$_3$) δ1.76 (m, 3H), 2.24 (m, 2H), 2.41 (s, 3H), 2.51 (m, 1H), 2.68 (m, 1H), 3.18 (m, 1H), 3.44 (m, 2H), 7.22 (m, 4H), 7.46 (m, 3H), 7.78 (m, 2H), 9.02 (br s, 1H), 12.97 (br s, 1H); IR (CHCl$_3$) 3385, 3035, 3000, 1620, 1570, 1485, 1450, 1215 cm$^{-1}$.

A solution of 0.4 g (1 mmol) of N-[3β-(4-Chlorophenyl)-tropane-2β-carboxylic]-N'-benzoyl-hydrazide and 0.8 g (2 mmol) of Lawesson's reagent in 10 ml toluene was refluxed for 4 h under nitrogen. The reaction mixture was cooled and solvent removed in vacuo to give a yellow residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [50% ether/triethylamine(9:1) in hexane] to obtain 0.23 g (58%) of pure thiadiazole (RTI-200) which was further purified by recrystallizing from ether: $^1$H NMR (CDCl$_3$) δ 1.75 (m, 3H), 2.20 (m, 3H), 2.32 (s, 3H), 3.30 (m, 3H), 3.78 (m, 1H), 6.86 (m, 2H), 7.08 (m, 2H), 7.43 (m, 3H), 7.97 (m, 2H); $^{13}$C NMR 25.55, 25.88, 34.60, 36.09, 41.55, 49.73, 61.48, 65.33, 127.59, 128.28, 128.78, 128.88, 130.37, 130.88, 132.19, 139.27, 168-29, 169.56; IR (CCl$_4$) 2940, 1490, 1460, 1340, 1245, 1100, 1010 cm$^{-1}$ The thiadiazole was converted into hydrochloride salt: $^1$H NMR (MeOD) δ 2.06 (m, 1H), 2.53 (m, 5H), 2.97 (s, 3H), 3.92 (m, 1H), 4.17 (m, 2H), 4.39 (m, 1H), 7.11 (m, 2H), 7.26 (m, 2H), 7.51 (m, 3H); 7.79 (m, 2H); mp 165-170° C.; Anal clacd. for $C_{22}H_{23}Cl_2N_3S.0.75H_2O$; C, 59.26; H, 5.54; N 9.42; Cl, 15.90; S, 7.19. Found: C, 59.27; H, 5.52; N, 9.40; Cl, 15.99; S 7.09; $[\alpha]_D$-42.81° (c, 0.16; MeOH).

Further elution gave 0.08 g (21%) as a second fraction which was characterized to be 3β-(4-chlorophenyl)-2α-(5-phenyl-1, 3,4-oxadiazol-2-yl)-tropane.

Example 6

3β-(4-Methylphenyl)-2β-(5-phenyl-1,3,4-thiadiazol-2-yl)-tropane Hydrochloride (RTI-199)

Reaction of 0.65 g (2.5 mmol) of 3β-(4-Methylphenyl)-tropane-2β-carboxylic acid as described above for preparation of amides gave after work up and purification by flash column chromatography [(50% CMA-80 in methylene chloride)] 0.48 g (51%) pure N-([3β-(4-Methylphenyl) Tropane-2β-carboxylic]-N'-benzoyl-hydrazide which was further purified by recrystallizing from ether/pet ether: $^1$H NMR (CDCl$_3$) δ 1.75 (m, 3H), 2.20 (m, 2H), 2.27 (s, 3H), 2.42 (s, 3H), 2.51 (m, 1H)$_1$ 2.67 (m, 1H), 3.18 (m, 1H), 3.47 (m, 2H), 7.11 (m, 4H), 7.48 (m, 3H), 7.81 (m, 2H), 9.06 (br s, 1H), 13.09 (br s, 1H); IR (CHCl$_3$) 3385, 30451, 1625, 1570, 1460, 1420, 1100 cm$^{-1}$;

Reaction of 0.29 g (0.75 mmol) of N-[3β-(4-Methylphenyl)-tropane-2β-carboxylic]-N'-benzoyl-hydrazide as described above for RTI-200 gave after work and purification by flash chromatography [40% ether/triethylamine(9:1) in hexane] 0.16 g (58%) of pure thiadiazole (RTI-199): $^1$H NMR (CDCl$_3$) δ 1.70 (m, 1H), 1.88 (m, 2H), 2.20 (s, 3H), 2.23 (m, 2H), 2.21 (s, 3H), 2.38 (m, 1H), 3.21 (m, 1H), 3.32 (m, 1H), 3.39 (m, 1H), 3.78 (m, 1H), 6.81 (m, 2H), 6.92 (m, 2H), 7.43 (m, 3H), 7.97 (m, 2H); $^{13}$C NMR 20.98, 25.65, 25.95, 34.79, 36.25, 41.65, 50.05, 61.68, 65.49, 127.32, 127.65, 128.89, 128.95, 130.29, 131.11, 135.94, 137.68, 168.83, 169.45; IR (CCl$_4$) 2935, 1510, 1450, 1250, 1120, 1100, 1060 cm$^{-1}$ The thiadiazole was converted into hydrochloride salt; $^1$H NMR (MeOD) δ 1.95 (m, 1H), 2.17 (s, 3H), 2.41 (m, 5H), 2.89 (s, 3H), 3.76 (m, 1H), 4.05 (m, 2H), 4.30 (m, 1H), 4.22 (m, 1H), 6.89 (m, 2H), 6.99 (m, 2H), 7.39 (m, 3H), 7.67 (m, 2H); mp 180-185° C.; Anal clacd. for C$_{23}$H$_{26}$ClN$_3$S.H$_2$O; C, 65.62; H, 6.46; N, 9.98; Cl, 18.42; S, 7.62. Found: C, 65.57; H, 6.63; N, 9.91; Cl, 18.24; S, 7.55; [α]$_D$–33.5° (c, 0.2; MeOH).

Further elution gave 0.04 g (15%) of a second fraction which was characterized to be 3β-(4-Methylphenyl)-2α(5-phenyl-1,3,4-oxadiazol-2-yl)-tropane.

Example 7

3β-(4-Chlorophenyl)-2β-(5-phenyl-oxazol-2-yl)-tropane Tartrate RTI-189)

Reaction of 0.73 g (2.5 mmol) of 3β-(4-Chlorophenyl)-tropane-2β carboxylic acid as described above for the preparation of amides gave after purification by flash column chromatography (15% CMA 80 in methylene chloride) 0.8 g (81%) of pure 3β-(4-Chlorophenyl)-tropane-2β-N-(phenyacyl)carboxamide: $^1$H NMR (CDCl$_3$) δ 1.71 (m, 3H), 2.19 (m, 2H), 2.39 (s, 3H), 2.46 (m, 1H), 2.58 (m, 1H), 3.13 (m, 1H), 3.43 (m, 2H), 4.74 (m, 2H), 7.13 (m, 4H), 7.49 (m, 2H), 7.59 (m, 1H), 7.96 (m, 2H), 10.57 (br s, 1H); IR (CHCl$_3$) 3135, 3010, 2930, 1695, 1650, 1590, 1530, 1485, 1450, 1355, 1220 cm$^{-1}$.

A solution of 0.725 g (1.83 mmol) of 3β-(4-Chlorophenyl)-tropane-2β-N(phenyacyl)carboxamide in 6 ml POCl$_3$ was heated at 125° C. under nitrogen for 2 hours. The reaction mixture was cooled and poured into ice and rendered basic to pH 7-8 using concentrated NH$_4$OH. To the ice cold aqueous layer was added 10 ml brine and extracted thrice with 10 ml methylene chloride. The organic layers were combined dried (NaSO$_4$), filtered, and the solvent removed in vacuo to 0.63 g crude oxazole. Purification of the crude by flash column chromatography [(40% ether/triethylamine 9:1) in hexane] gave 0.34 g (49%) of pure oxazole (RTI-189) which was further purified by recrystallizing from ether/petroleum ether: $^1$H NMR (CDCl$_3$) 1.79 (m, 3H), 2.22 (s, 3H), 2.27 (m, 2H), 2.66 (m, 1H), 3.27 (m, 1H), 3.40 (m, 2H), 3.53 (m, 1H), 7.11 (s, 1H), 7.16 (s, 4H) 7.31 (m, 5H); IR (CHCl3) 2950, 1540, 1490, 1445, 1350, 1120, 1090 CM$^{-1}$; [α]$_D$–70.37° (c, 0.19; CHCl$_3$).

The oxazole was converted into tartrate salt: $^1$H NMR (MeOD) 2.14 (m, 1H), 2.54 (m, 5H), 2.96 (s, 3H), 3.75 (m, 2H), 4.12 (m, 1H), 4.25 (m, 1H), 4.41 (s, 2H), 7.05 (m, 2H), 7.29 (m, 7H), 7.45 (s, 1H), 7.43 (s, 1H); mp 126° C. (dec); Anal calcd for C$_{27}$H$_{29}$ClN$_2$O$_7$.0.75H$_2$O; C, 59.78; H, 5.67; N, 5.16; Cl, 6.54. found: C, 59.78; H, 5.58; N, 4.93; Cl, 6.31; [α]$_D$+101.43° (c, 0.21; CH$_3$OH).

Example 8

3β-(4-Methylphenyl)-2β-(5-phenyl-oxazol-2-yl)-tropane Tartrate (RTI-178)

Reaction of 0.52 g (2 mmol) of 3β-(4-Methylphenyl)-tropane-2β-carboxylic acid as described above for preparation of amides gave after work up and purification by flash column chromatography (15% CMA in methylene chloride) 0.54 g (72%) of pure 3β-(4-Methylphenyl)-tropane-2β-N-(phenyacyl)carboxamide: $^1$H NMR (CDCl$_3$) δ 1.73 (m, 3H), 2.14 (m, 2H), 2.26 (s, 3H), 2.40 (s, 3H), 2.47 (m, 1H), 2.59 (m, 1H), 3.14 (m, 1H), 3.42 (m, 2H), 4.74 (m, 2H), 7.05 (m, 4H), 7.48 (m, 2H), 7.59 (m, 2H), 7.97 (m, 2H), 10.62 (br s, 1H); IR (CHCl$_3$) 3155, 3005, 2930, 1690, 1650, 1520, 1450, 1355, 1215 cm$^{-1}$ Reaction of 0.5 g (1.33 mmol) of 3β-(4-Methylphenyl)-tropane-2β-N-(phenyacyl)carboxamide as described above for RTI-189 gave after workup and purification by flash column chromatography [(40% (ether/triethylamine 9:1) in hexane] 0.1 g (31%) RTI-158 as a first fraction. Further elution gave 0.19 g (42%) of pure oxazole RTI-178: $^1$H NMR (CDCl$_3$) 1.8 (m, 3H), 2.18 (m, 2H), 2.21 (s, 3H), 2.22 (s, 3H), 2.67 (m, 1H), 3.28 (m, 1H), 3.42 (m, 2H), 3.53 (m, 1 H), 6.98 (m, 2H), 7.11 (m, 3H), 7.30 (m, 5H).

The oxazole was crystallized as the tartrate salt: $^1$H NMR (MeOD) 1.99 (m, 1H), 2.19 (s, 3H), 2.54 (m, 5H), 2.95 (s, 3 H), 3.74 (m, 2H), 4.13 (m, 1H), 4.26 (m, 1H), 4.4 (s, 2H), 6.91 (m, 2H), 7.0 (m, 2H), 7.25 (m, 2H), 7.33 (m, 3H), 7.43 (s, 1H); mp 175-181 C; Anal clacd. for C$_{28}$H$_{32}$N$_2$O$_7$.1H$_2$O; C, 63.87; H, 6.51; N, 5.32. Found: C, 64.21; H, 6.40; N, 5.19; [α]$_D$–104.04° (c, 0.6; CH$_3$OH).

Example 9

3β-(4-Chlorophenyl)-2β-(5-phenylthiazol-2-yl)-tropane Hydrochloride (RTI-219)

To a solution of 0.74 g (1.86 mmol) of 3β-(4-Chlorophenyl)-tropane-2β-N-(phenyacyl)carboxamide and 1.51 g (7.45 mmol) of Lawesson's reagent in 18 ml of toluene was refluxed under N$_2$ for 5 hours. The reaction mixture was cooled and solvent removed in vacuo to give crude residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [(40% (ether/triethylamine 9:1) in hexane] to give 0.21 g (30%) of pure thiazole RTI-219: $^1$H NMR (CDCl$_3$) 1.61 (m, 1H), 1.82 (m, 2 H), 2.22 (m, 2H), 2.34 (s, 3H), 2.39 (m, 1H), 3.28 (m, 2H), 3.39 (m, 1H), 3.49 (m, 1H), 6.8 (m, 2H) 7.07 (m, 2H). 7.32 (m, 3H), 7.57 (m, 2H), 7.60 (s, 1H); $^{13}$C NMR (MeOD) 25.51, 25.99, 35.01, 36.92, 41.72, 52.97, 61.58, 65.70, 126.45, 127.60, 128.13, 128.89, 129.05, 131.91, 132.43, 136.11, 139.91, 140.27, 168.97; IR (CHCl$_3$) 2945, 1590, 1485, 1445, 1350, 1125, 1090. cm$^{-1}$.

The thiazole was converted into hydrochloride salt: $^1$H NMR (MeOD) 1.99 (m, 1H), 2.51 (m, 5H), 2.93 (s, 3H), 3.79 (m, 2H), 4.15 (m, 1H), 4.28 (m, 1H), 7.02 (d, J=8.5 Hz, 2H) 7.21 (d, J=8.5 Hz, 2H), 7.39 (m, 5H), 8.06 (s, 1H); mp 228-230° C.; Anal clacd. for C$_{23}$H$_{24}$ClN$_2$S.H$_2$O; C, 61.47; H, 5.83; N, 6.23; S, 7.13; Cl, 15.78. Found: C, 61.61; H, 5.76; N, 6.20; S, 7.51; Cl, 15.84; [α]$_D$+27.430 (c, 0.11; CH$_3$OH).

Example 10

3β-(4-Chlorophenyl)-2β-(benzothiazol-2-yl)-tropaneHydrochloride (RTI-202)

Reaction of 0.59 g (2 mmol) of 3β-(4-Chlorophenyl)-tropane-2β-carboxylic acid as described above for preparation of amides gave after purification of the crude by flash column chromatography (50% CMA-80 in methylene chloride) 0.3 g (41%) of pure RTI-202 which was further purified by recrystallizing from ether/hexane: $^1$H NMR (CDCl$_3$) δ 1.65 (m, 1H), 1.87 (m, 2H), 2.24 (m, 2H), 2.34 (s, 3H), 2.41 (m, 1H), 3.28 (m, 2H), 3.40 (m, 1H), 3.62 (m, 1H), 6.8 (m, 2H), 6.81 (m, 2H), 7.29 (m, 2H); 7.70 (m, 1H), 7.84 (m, 1H); $^{13}$C NMR (CDCl$_3$) δ 25.58, 26.07, 35.40, 36.95, 41.56, 53.09, 61.57, 65.47, 120.95, 122.42, 124.11, 125.20, 128.05, 129.03, 131.87, 136.72, 139.91, 151.33, 171.11; IR (CHCl$_3$) 2940, 2795, 1495, 1445, 1305, 1130, 1105, 1015, 907 CM$^{-1}$; [α]$_D$–233.89° (c, 0.09; CHCl$_3$).

The benzothiazole was converted into hydrochloride salt: $^1$H NMR (MeOD) δ 2.02 (m, 1H), 2.43 (m, 4H), 2.89 (m, 1H), 2.98 (s, 3H), 3.90 (m, 2H), 4.23 (m, 1H), 4.34 (m, 1H), 7.02 (m, 2H), 7.13 (m, 2H), 7.45 (m, 2H), 7.81 (m, 1H), 8.16 (m, 1H); mp 140-150° C. (dec); Anal clacd. for C$_{21}$H$_{22}$Cl$_2$N$_2$S.0.75H$_2$O C, 60.21; H, 5.65; N, 6.69; Cl, 16.93; S, 7.65. Found: C, 60.14; H, 5.74; N, 6.60; Cl, 16.89; S, 7.71; [α]$_D$–1 72.49° (c 0.28; MeOH).

Example 11

3β-(4-Chlorophenyl)-tropane-2β-nitrile (RTI-161)

To a solution of 0.95 g (3.5 mmol) of 3β-(4-Chlorophenyl)-tropane-2β-carboxamide in 20 ml dry THF was added 0.56 ml (7 mmol) pyridine. To the resulting solution at room temperature was added dropwise with stirring under nitrogen 0.35 ml (4.2 mmol) of trifluoroacetic anhydride. The reaction was stirred at room temperature for 30 minutes, and quenched with 10 ml water. The solvent was removed under vacuo and the residue was taken in 10 ml saturated aqueous K$_2$CO$_3$ and extracted thrice with 10 ml CHCl$_3$. The organic layers were combined and washed with 20 ml brine dried (NaSO$_4$), filtered, and the solvent removed in vacuo to give 0.26 g crude product. Purification of the crude by flash column chromatography (10% CMA in methylene chloride) gave 0.68 g (77%) of pure nitrile RTI-161 which was recrystallized from methylene chloride and hexane: $^1$H NMR (CDCl$_3$) δ 1.70 (m, 3H), 2.22 (m, 3H), 2.35 (s, 3H), 2.80 (m, 1H), 3.04 (m, 1H), 3.34 (m, 1H), 3.43 (m, 1H), 7.26 (m, 4H); IR (CHCl$_3$) 3700, 2950, 2225, 1490, 1470, 1090, 900 cm$^{-1}$; mp 167-173° C.; Anal clacd. for C$_{15}$H$_{18}$Cl$_2$N$_2$.0.75H$_2$O; C, 57.98; H, 6.32; N, 9.02; Cl, 22.82. found: C, 58.22; H, 6.12; N, 8.48; Cl, 22.89; [α]$_D$–73.33° (c, 0.48; MeOH).

Example 12

3β-(4-Methylphenyl)-tropane-2β-nitrile Hydrochloride (RTI-158)

Reaction of 0.26 g (1 mmol) of 3β-(4-Methylphenyl)-tropane-2β-carboxamide as described above for RTI-161 gave after work up and purification 0.16 g (67%) of pure nitrile (RTI-158): $^1$H NMR (CDCl$_3$) δ 1.68 (m, 3H), 2.18 (m, 3H), 2.32 (s, 3H), 2.35 (s, 1H), 2.82 (m, 1H), 3.02 (m, 1H), 3.36 (m, 1H), 3.43 (m, 1H), 7.18 (m, 4H); IR (CHCl$_3$) 3675, 3000, 2950, 2200, 1600, 1510, 1450, 1350, 1220, 1100 cm$^{-1}$.

The crude product was crystallized as the HCl salt: $^1$H NMR (MeOH) δ 2.08-2.58 (m, 9H), 2.92 (s, 3H), 3.54 (m, 1H), 3.69 (br s, 1H), 4.12 (br s, 1H), 4.29 (m, 1H), 7.21 (m, 4H); mp 270° C. (dec.); Anal clacd. for C$_{16}$H$_{21}$ClN$_2$; C, 69.42; H, 7.65; N, 10.12; Cl, 12.81. Found: C, 69.31; H, 7.70; N, 10.12; Cl, 12.81; [α]$_D$–76.40 (c, 0.5; MeOH).

Example 13

3β-(4-Chlorophenyl)-tropane-2β-tetrazole (RTI-163)

To a solution of 0.13 g (0.5 mmol) of RTI-161 in 5 ml dry THF was added 0.28 ml (5 mmol) azidotrimethylsilane and the mixture was placed in a PTFE-lined autoclave. The solution was heated to 150° C. for 24 hours in an oil bath. The reaction mixture was cooled and transferred using MeOH. The solvent was removed in vacuo to give a brownish residue. Purification of the crude by flash column chromatography (20%-50% CMA in methylene chloride) gave 0.05 g (33%) of pure tetrazole (RTI-163): $^1$H NMR (CDCl$_3$+1 drop MeOD) δ 1.73 (m, 1H), 2.44-2.02 (m, 4H), 2.6 (m, 1H), 2.68 (s, 3H), 3.33 (m, 1H), 3.65 (m, 1H), 3.73 (m, 1H), 3.97 (m, 1H), 6.68 (d, J=8 Hz, 2H), 7.07 (d, J=8 Hz, 2H); mp 296-300° C.; Anal clacd. for C$_{15}$H$_{18}$ClN$_5$.0.75H$_2$O; C, 56.78; H, 6.19; N, 22.07; Cl, 11.17. Found: C, 56.69; H, 6.22; N, 22.09; Cl, 11.15; [α]$_D$–124.94° (c, 0.39; MeOH).

Example 14

3β-(4-Methylphenyl)-tropane-2β-tetrazole Hydrochloride (RTI-157)

Reaction of 0.12 g (0.5 mmol) of RTI-158 as described above for RTI-163 gave after workup and purification of the crude by flash column chromatography (100% CMA) 0.14 g (88%) of pure tetrazole (RTI-157): $^1$H NMR (CDCl$_3$+1 drop MeOD) δ 1.8 (m, 1H), 2.14 (s, 3H), 2.35 (m, 5H), 2.71 (s, 3H), 3.36 (m, 1H), 3.75 (m, 2H), 4.02 (m, 1H), 6.48 (d, J=8 Hz, 2H), 6.82 (d, J=8 Hz, 2H).

The purified product was converted into HCl salt: $^1$H NMR (MeOD) δ 2.01 (m, 1H), 2.27 (s, 3H), 2.69 (m, 5H), 2.97 (s, 3H), 3.81 (m, 2H), 4.18 (m, 2H), 5.5 (s, 1H), 6.76 (d, J=8 Hz, 2H), 7.02 (d, J=8 Hz, 2H); mp 212**C (dec); Anal calcd for C$_{16}$H$_{23}$Cl$_2$N$_5$.0.25H$_2$O; C, 53.26; H, 6.56; N, 19.41. Found: C, 53.41; H, 6.50; N, 19.02; [α]$_D$–110.97° (c, 0.16; MeOH).

Example 15

3β-(4-Chlorophenyl)-2β-(3-methylisoxazol-5-yl) tropane Hydrochloride (RTI-165)

A solution of n-butyl lithium in hexane 5.9 ml (2.5 M. 14.6 mmol) was added to a stirred solution of acetone oxime 0.55 g (7.3 mmol) in dry THF (15 ml) at 0° C. under nitrogen. After 1 hour, a solution of 1.65 g (5.62 mmol) 3β-(4-Chlorophenyl)-2β-(carbomethoxy)tropane in 10 ml dry was added dropwise with stirring at 0° C. The solution was allowed to warm to room temperature over 18 hours. The mixture was poured into a stirred solution of concentrated sulfuric acid (3.2 g) in THF (15 ml) and water (4 ml) and was heated under reflux for 1 hour. The cooled solution was made basic using saturated aqueous K$_2$CO$_3$ (10 ml) and extracted thrice with 10 ml methylene chloride. The combined organic layers were dried (Na$_2$SO$_4$), filtered and solvent removed in vacuo to give 1.8 g of crude isoxazole. Purification of the crude residue by flash column chromatography (10% CMA in methylene chloride) gave 0.74 g (46%) of pure isoxazole RTI-165 which was further purified by crystallization from methylene chloride/hexane: $^1$H NMR (CDCl$_3$) δ 1.71 (m, 3H), 2.10 (m, 3H), 2.18 (s, 3H), 2.24 (s, 3H), 3.20 (m, 2H), 3.32 (m, 2H), 6.18 (s, 1H), 6.9 (d, J=8 Hz, 2H), 7.14 (d, J=8, Hz, 2H); IR (CCl$_4$) 2950, 1590, 1490, 1420, 1350, 1020, 910 cm$^{-1}$; mp 154-156° C.; Anal clacd. for $C_{18}H_{21}N_2OCl$; C, 68.28; H, 6.68; N, 8.84; Cl, 11.19. Found: C, 68.22; H, 6.69; N, 8.87; Cl, 11.19; $[\alpha]_D$–125.58° (c, 0.43; MeOH).

The isoxazole was crystallized as the hydrochloride salt: $^1$H NMR (MeOD) δ 2.04 (s, 3H), 2.19 (m, 1H), 2.30 (m, 1H), 2.48 (m, 2H), 2.60 (m, 1H), 2.70 (m, 1H), 2.90 (s, 3H), 3.68 (m, 1H), 3.81 (m, 1H), 4.04 (m, 1H), 4.15 (m, 1H), 5.55 (s, 1H), 7.04 (d, J=8 Hz, 2H), 7.14 (d, J=8 Hz, 2H); mp >235° C. (dec); Anal clacd. for $C_{18}H_{22}Cl_2N_2O$; C, 61.19; H, 6.28; N, 7.93; Cl, 20.07. Found: c, 60.98; H, 6.38; N, 7.91; Cl, 19.96; $[\alpha]_D$–102.89° (c, 0.46; MeOH).

Example 16

3β-(4-Methylphenyl)-2β-(3-methylisoxazol-5-yl) tropane Hydrochloride (RTI-171)

Reaction of 1.09 g (4 mmol) of 3β-(4-Methylphenyl)-2β-(carbomethoxy)tropane as described above for RTI-165 gave after workup 1.21 g crude isoxazole. Purification of the crude by flash column chromatography (15% CMA in methylene chloride) gave 0.73 g (62%) pure isoxazole (RTI-171): $^1$H NMR (CDCl$_3$) δ 1.73 (m, 3H), 2.11 (m, 3H), 2.17 (s, 3H), 2.23 (s, 3H), 2.25 (s, 3H), 3.20 (m, 2H), 3.32 (m, 2H), 6.13 (s, 1H), 6.97 (m, 4H); IR (CCl$_4$) 2935, 2785, 1590, 1510, 1460, 1421, 1350, 1125, 1010, 910 cm$^{-1}$.

The isoxazole was crystallized as the hydrochloride salt: $^1$H NMR (MeOD) δ 2.01 (s, 3H), 2.24 (s, 3H), 2.32 (m, 2H), 2.42 (m, 4H), 2.81 (s, 3H), 3.61 (m, 1H), 3.78 (m, 1H), 4.03 (m, 1H), 4.15 (m, 1H), 5.45 (s, 1H), 6.96 (m, 4H); Mp 277° C.; Anal clacd. for $C_{19}H_{25}ClN_2O$; C, 68.55; H, 7.57; N, 8.42; Cl, 10.65. found: C, 68.65; H, 7.62; N, 8.42; Cl, 10.56; $[\alpha]_D$–107.28° (c, 0.71; MEOH).

Example 17

3β-(4-Iodophenyl)-2β-(3-methylisoxazol-5-yl)tropane Hydrochloride (RTI-180)

Reaction of 0.73 g (1.9 mmol) of 3β-(4-Iodophenyl)-2β-(carbomethoxy)tropane as described above for RTI-165 gave after workup 0.77 g of crude isoxazole. Purification of the crude by flash column chromatography (5% CMA80 in methylene chloride) gave 0.37 g (49%) of pure isoxazole RTI-180: $^1$H NMR (CDCl$_3$) δ 1.71 (m, 3H), 2.12 (m, 3H), 2.18 (s, 3H), 2.24 (s, 3H), 3.17 (m, 2H), 3.33 (m, 2H), 6.18 (s, 1H), 6.74 (m, 2H), 7.49 (m, 2H); IR (CHCl$_3$) 2940, 1600, 1485, 1450, 1420, 1355 cm$^{-1}$.

The isoxazole was crystallized as the hydrochloride salt: $^1$H NMR (MeOD) δ 2.11 (s, 3H), 2.50 (m, 6H), 2.89 (s, 3H), 3.70 (m, 1H), 3.90 (m, 1H), 4.14 (m, 1H), 4.22 (m, 1H), 5.66 (s, 1H), 6.96 (m, 2H), 7.56 (m, 2H); mp >235° C. (dec); Anal calcd for $C_{18}H_{22}ClIN_2O \cdot 0.25H_2O$ C, 48.12; H, 5.05; N, 6.24; Cl, 15.79; I, 56.50. Found: C, 47.84; H, 5.05; N, 6.19; Cl, 15.77; I, 56.46; $[\alpha]_D$–94.570 (c, 0.39; MeOH).

Example 18

3β-(4-Chlorophenyl)-2β-(3-phenylisoxazol-5-yl) tropane Hydrochloride (RTI-177)

Reaction of 1.18 g (4 mmol) of 3β-(4-Chlorophenyl)-2β-(carbomethoxy)tropane as described above for RTI-165 gave after work up 1.46 g of crude isoxazole. Purification of the crude by flash column chromatography [20% (ether/triethylamine 9:1) in hexane] gave 0.75 g (50%) of pure isoxazole RTI-177 which was further purified by crystallizing from ether/petroleum ether: $^1$H NMR (CDCl$_3$) δ 1.74 (m, 3H), 2.22 (m, 3H), 2.27 (s, 3H), 3.24 (m, 2H), 3.36 (m, 2H), 6.80 (s, 1H), 6.94 (m, 2H), 7.12 (m, 2H), 7.40 (m, 3H), 7.76 (m, 2H); IR (CHCl$_3$) 2940, 1600, 1590, 1490, 1450, 1405, 1350 cm$^{-1}$.

The isoxazole was crystallized as the hydrochloride salt: $^1$H NMR (MeOD) δ 2.35 (m, 6H), 2.84 (s, 3H), 3.73 (m, 1H), 4.09 (m, 1H), 4.21 (m, 1H), 6.12 (s, 1H), 7.14 (m, 4H), 7.34 (m, 3H), 7.57 (m, 2H); mp 287° C.; Anal clacd. for $C_{23}H_{24}Cl_2N_2O \cdot 0.25H_2O$ C, 65.79; H, 5.88; N 6.67; Cl, 16.89. Found: C, 65.94; H, 5.79; N, 6.68; Cl, 17.00; $[\alpha]_D$–97.5° (c, 0.28; MeOH).

Example 19

3β-(4-Methylphenyl)-2β-(3-phenylisoxazol-5-yl) tropane Hydrochloride (RTI-176)

Reaction of 1.09 g (4 mmol) of 3β-(4-Methylphenyl)-2β-(carbomethoxy)tropane as described above for RTI-165 gave after work up 1.56 g of crude isoxazole. Purification of the crude by flash column chromatography [25% (ether/triethylamine 9:1) in hexane] gave 1.1 g (77%) of pure isoxazole RTI-176 which was further purified by crystallizing from methylene chloride/hexane: $^1$H NMR (CDCl$_3$) δ 1.76 (m, 3H), 2.23 (m, 3H), 2.24 (s, 3H), 2.27 (s, 3H), 3.23 (m, 2H), 3.36 (m, 2H), 6.74 (s, 1H), 6.93 (m, 4H), 7.41 (m, 3H), 7.76 (m, 2H); IR (CCl$_4$) 2935, 1590, 1455, 1410, 1215 cm$^{-1}$ The isoxazole was crystallized as the hydrochloride salt: $^1$H NMR (MeOD) δ 2.08 (m, 1H), 2.15 (s, 3H), 2.45 (m, 5H), 2.84 (s, 3H), 3.68 (m, 1H), 3.88 (m, 1H), 4.07 (m, 1H), 4.22 (m, 1H), 5.97 (s, 1H), 7.0 (m, 4H), 7.33 (m, 3H), 7.54 (m, 2H); mp 270-295° C. (dec); Anal clacd. for $C_{24}H_{27}ClN_2O$; C, 72.99; H, 6.89; N, 7.10; Cl, 8.98. Found: C, 72.91; H, 6.91; N, 7.15; Cl, 8.98; $[\alpha]_D$–102.22 (c, 0.68; MeOH).

Example 20

3β-(4-Iodophenyl)-2β-(3-phenylisoxazol-5-yl)tropane Hydrochloride (RTI-181)

Reaction of 0.73 g (1.9 mmol) of 3β-(4-Iodophenyl)-2β-(carbomethoxy)tropane as described above for RTI-181 gave after workup 1.46 g of crude isoxazole. Purification of the crude by flash column chromatography [20% (ether/triethylamine 9:1) in hexane] gave 0.5 g (56%) of pure isoxazole RTI-181 which was further purified by crystallizing from methylene chloride/hexane: $^1$H NMR (CDCl$_3$) δ 1.72 (m, 3H), 2.15 (m, 2H), 2.28 (s, 3H) 3.22 (m, 2H), 3.35 (m, 2H), 6.74 (m, 2H), 6.79 (s, 1H), 7.44 (m, 5H), 7.75 (m, 2H); IR (CHCl$_3$) 2940, 1580, 1480, 1475, 1450, 1400, 1355, 1005 cm$^{-1}$ The isoxazole was crystallized as the hydrochloride salt: 1H NMR (MeOD) δ 2.54 (m, 6H), 2.92 (s, 3H), 3.79 (m, 1H), 4.05 (m, 1H), 4.19 (m, 1H), 4.33 (m, 1H), 6.18 (s, 1H), 7.02 (m, 2H), 7.43 (m, 3H), 7.63 (m, 4H); mp >267° C. (dec); Anal clacd. for $C_{23}H_{24}ClIN_2O \cdot 0.5H_2O$ C, 53.55; H, 4.89; N, 5.43; Cl, 13.75; I, 49.21. Found: C, 53.75; H, 4.87; N, 5.41; Cl, 13.68; I, 48.95; $[\alpha]_D$–91.11° (c, 0.43; MeOH).

Example 21

Biochemistry of 3β-(Substituted phenyl)-2β-(heterocyclic)tropanes

Inhibition of radioligand binding data at the dopamine, serotonin, and norepinephrine transporters are listed in Table II, III and IV.

TABLE II

3β-(Substituted phenyl)-2β-(heterocyclic)tropanes

A

| Code Name | Het | X | DA [$^3$H]-WIN 35,428 | NE [$^3$H]-nisoxetine | 5-HT [$^3$H]-paroxetine | NE/DA Ratio | 5-HT/DA Ratio |
|---|---|---|---|---|---|---|---|
| RTI-163 | 4-methyl-1,2,3-triazol-1-yl | Cl | 911 ± 6.1 | 17,386 ± 2050 | 5456 ± 64 | 19 | 6 |
| RTI-157 | 4-methyl-1,2,3-triazol-1-yl | CH$_3$ | 1557 ± 196 | 32,478 ± 2078 | 43,574 ± 5420 | 21 | 28 |
| RTI-165 | 5-methylisoxazol-3-yl | Cl | 0.59 ± 0.04 | 181 ± 12 | 572 ± 58 | 307 | 970 |
| RTI-171 | 5-methylisoxazol-3-yl | CH$_3$ | 0.93 ± 0.09 | 254 ± 31 | 3818 ± 346 | 273 | 4105 |
| RTI-180 | 5-methylisoxazol-3-yl | I | 0.73 ± 0.04 | 67.9 ± 5.25 | 36.4 ± 5.0 | 93 | 498 |
| RTI-177 | 5-phenylisoxazol-3-yl | Cl | 1.28 ± 0.18 | 504 ± 29 | 2418 ± 136 | 393 | 1889 |
| RTI-176 | 5-phenylisoxazol-3-yl | CH$_3$ | 1.58 ± 0.02 | 398 ± 18 | 5110 ± 187 | 251 | 3234 |
| RTI-181 | 5-phenylisoxazol-3-yl | I | 2.57 ± 0.14 | 868 ± 95 | 100 ± 9.0 | 337 | 39 |
| RTI-189 | 2-methyl-5-phenyloxazol-5-yl | Cl | 19.7 ± 1.98 | 496 ± 42 | 1116 ± 107 | 25 | 57 |
| RTI-178 | 2-methyl-5-phenyloxazol-5-yl | CH$_3$ | 35.4 ± 1.74 | 677 ± 68 | 1699 ± 167 | 19 | 48 |
| RTI-188 | 2-methyl-5-phenyl-1,3,4-oxadiazol-5-yl | Cl | 12.6 ± 1.03 | 929 ± 88 | 3304 ± 196 | 73 | 262 |
| RTI-195 | 2-methyl-5-phenyl-1,3,4-oxadiazol-5-yl | CH$_3$ | 47.5 ± 4.76 | 1310 ± 37 | 23,310 ± 822 | 28 | 491 |
| RTI-194 | 2,5-dimethyl-1,3,4-oxadiazol-5-yl | CH$_3$ | 4.45 ± 0.12 | 253 ± 19 | 4885 ± 155 | 57 | 1098 |
| RTI-200 | 2-methyl-5-phenyl-1,3,4-thiadiazol-5-yl | Cl | 15.3 ± 2.43 | 4142 ± 466 | 18,417 ± 1509 | 271 | 1203 |
| RTI-199 | 2-methyl-5-phenyl-1,3,4-thiadiazol-5-yl | CH$_3$ | 35.9 ± 3.4 | 24,321 ± 3822 | 51,460 ± 4513 | 677 | 1434 |
| RTI-202 | 2-methylbenzothiazol-2-yl | Cl | 1.37 ± 0.14 | 403 ± 30 | 1119 ± 120 | 294 | 817 |
| RTI-219 | 2-methyl-5-phenylthiazol-5-yl | Cl | 5.71 ± 0.36 | 8563 ± 824 | 10,342 ± 76 | 1500 | 1811 |

TABLE III

Comparison of Transporter Binding Potencies

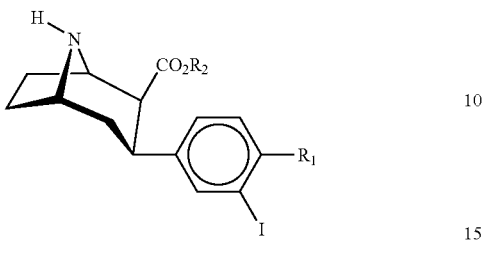

| | | | IC$_{50}$ (nM) | | |
|---|---|---|---|---|---|
| RTI No. | R$_1$ | R$_2$ | 5-HT [$^3$H]Paroxetine | DA [$^3$H]WIN 35,428 | NE [$^3$H]Nisoxetine |
| 279 | CH$_3$ | CH$_3$ | 1.00 ± 0.39 | 5.98 ± 0.48 | 74.3 ± 3.8 |
| 353 | C$_2$H$_5$ | CH$_3$ | 0.69 ± 0.07 | 331 ± 17 | 148 ± 9.2 |
| Paroxetine* | | | 0.28 ± 0.02 | 623 ± 25 | 313 |

5-HT = serotonin
DA = dopamine
NE = norepinephrine
*Aropax: Seroxat; see Merck Index.

TABLE IV

3β-(Substituted phenyl)-2β-(substituted)tropanes

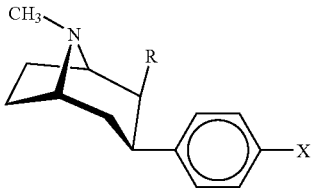

| | | | IC$_{50}$ (nM) | |
|---|---|---|---|---|
| Code Name | R | X | DA [$^3$H]-WIN 35.428 | NE [$^3$H]-nisoxetine | 5-HT [$^3$H]-paroxetine |
| RTI-93 | CH$_2$OH | Cl | 1.53 ± 0.15 | 43.8 ± 8.4 | 204 ± 16 |
| RTI-99 | CH$_2$OH | Br | 1.49 ± 0.05 | | 51 ± 4.6 |
| RTI-100 | CH$_2$OH | F | 47 ± 4.6 | | 4741 ± 335 |
| RTI-101 | CH$_2$OH | I | 2.2 ± 0.19 | | 26 ± 3.2 |
| RTI-102 | CO$_2$H | I | 474 ± 57 | 43,400 ± 5500 | 1928 ± 120 |
| RTI-103 | CO$_2$H | Br | 278 ± 43 | 17,400 ± 1400 | 3070 ± 206 |
| RTI-104 | CO$_2$H | F | 2744 ± 141 | >100,000 | >100,00 |
| RTI-105 | CH$_2$OAc | Cl | 1.60 ± 0.05 | 127 ± 5.9 | 143 ± 25 |
| RTI-108 | CH$_2$Cl | Cl | 2.64 ± 0.31 | 129 ± 15 | 98 ± 8.7 |
| RTI-123 | CH$_2$OCOC$_6$H$_5$ | Cl | 1.78 ± 0.09 | 393 ± 30 | 3.53 ± 0.58 |
| RTI-131 | CH$_2$NH$_2$ | CH$_3$ | 10.5 ± 1.7 | 120 ± 20 | 855 ± 52 |
| RTI-132 | CH$_2$N(CH$_3$)$_2$ | CH$_3$ | 3.48 ± 0.11 | 137 ± 11 | 208 ± 18 |
| RTI-139 | CH$_3$ | Cl | 1.67 ± 0.13 | 57 ± 2.6 | 85 ± 9.3 |
| RTI-145 | CH$_2$OCO$_2$CH$_3$ | Cl | 9.6 ± 0.42 | 1478 ± 96 | 2930 ± 181 |
| RTI-158 | CN | CH$_3$ | 57 ± 7.3 | 1624 ± 136 | 5095 ± 315 |
| RTI-161 | CN | Cl | 13.1 ± 0.76 | 2516 ± 253 | 1887 ± 134 |
| RTI-164 | CH$_2$NHCH$_3$ | CH$_3$ | 13.6 ± 2.03 | 280 ± 19 | 2246 ± 94 |
| RTI-230 | —C(CH$_3$)=CH$_2$ | Cl | 1.28 ± 0.17 | 141 ± 16 | 57 ± 5.0 |
| RTI-239 | CH(CH$_3$)$_2$ | CH$_3$ | 0.61 ± 0.07 | 35.6 ± 2.57 | 114 ± 3.69 |

TABLE IV-continued

3β-(Substituted phenyl)-2β-(substituted)tropanes

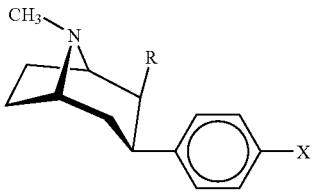

| | | | IC$_{50}$ (nM) | | |
|---|---|---|---|---|---|
| Code Name | R | X | DA [$^3$H]-WIN 35.428 | NE [$^3$H]-nisoxetine | 5-HT [$^3$H]-paroxetine |
| RTI-240 | CH(CH$_3$)$_2$ | Cl | 1.38 ± 0.03 | 84.5 ± 3.09 | 38.4 ± 2.31 |
| RTI-241 | CH$_2$CO$_2$CH$_3$ | CH$_3$ | 1.02 ± 0.06 | 124 ± 356 | 618 ± 28 |

This invention has been described in both generic terms, and by reference to specific description. No specific description or example is considered binding, unless so identified. Alternate forms and methods will occur to those of ordinary skill in the art, without the exercise of inventive faculty, and remain within the scope of this invention, save as limited by the claims set forth below.

What is claimed is:

1. A 2β,3β-cis substituted compound having the formula:

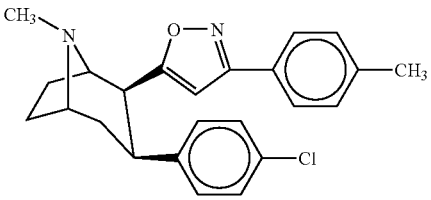

or a salt thereof.

2. The compound of claim 1, which is in the form an HCl salt.

* * * * *

UNITED STATES PATENT AND TRADEMARK OFFICE
CERTIFICATE OF CORRECTION

PATENT NO. : 7,291,737 B2  Page 1 of 7
APPLICATION NO. : 10/986352
DATED : November 6, 2007
INVENTOR(S) : Michael J. Kuhar et al.

It is certified that error appears in the above-identified patent and that said Letters Patent is hereby corrected as shown below:

Column 1, line 22, "5,413,779, and a which is a Continuation-in-part"
    should read -- 5,413,779, which is a Continuation-in-part --;
  line 25, "Application No. PCT/US91/05553, filed on Aug. 7,"
    should read -- Application No. PCT/US91/05553, filed on Aug. 9, --.

Column 2, lines 1-13, "

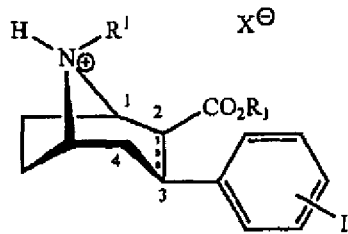

2

"

should read --

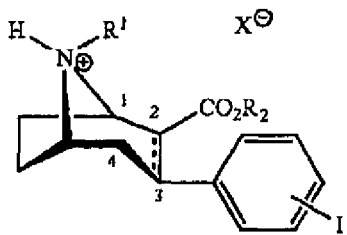

--;

Column 2, line 65, "24, 1995 Dec. 10, 1993, also incorporated herein by"
    should read -- 24, 1995, also Dec. 10, 1993, also incorporated herein by --.

UNITED STATES PATENT AND TRADEMARK OFFICE
CERTIFICATE OF CORRECTION

PATENT NO.        : 7,291,737 B2                                    Page 2 of 7
APPLICATION NO.   : 10/986352
DATED             : November 6, 2007
INVENTOR(S)       : Michael J. Kuhar et al.

It is certified that error appears in the above-identified patent and that said Letters Patent is hereby corrected as shown below:

Column 3, lines 13-15, "                                              "

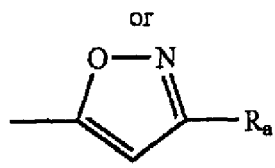

should read  --                                              --.

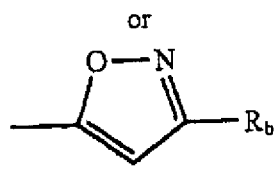

Column 5, lines 3-6,    "R₁, X, Y, Z are defined
                        above and M = $(CH_2)_x$
                        —CH=CH—
                        —C C— should read -- $R_1$, X, Y, Z are defined --;
                  above and M = $(CH_2)_x$
                    X = 1-8
                    —CH=CH—
                    —C C— line 45, "features of the invention that will become here in after"
            should read -- features of the invention that will become hereinafter --;
        line 64, "obtained from the tropane acid was treated to obtain nitrites"
            should read -- obtained from the tropane acid was treated to obtain
                  nitriles --.

UNITED STATES PATENT AND TRADEMARK OFFICE
CERTIFICATE OF CORRECTION

PATENT NO.         : 7,291,737 B2
APPLICATION NO. : 10/986352
DATED                  : November 6, 2007
INVENTOR(S)       : Michael J. Kuhar et al.

It is certified that error appears in the above-identified patent and that said Letters Patent is hereby corrected as shown below:

Column 6, lines 32-40, "                                                                                                "

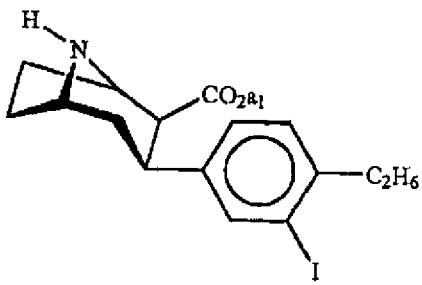

should read --

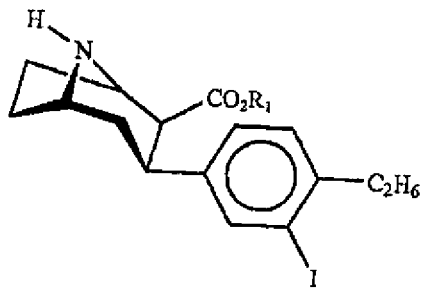

--.

Column 7, line 32, "pyridine in THF to the nitrites"
    should read -- pyridine in THF to the nitriles --.

Column 8, line 11, "and $^{186}$Re.c," should read -- and $^{186}$Re.c. --;
    line 41, "stratum, cerebral cortex,"
        should read -- striatum, cerebral cortex, --.

UNITED STATES PATENT AND TRADEMARK OFFICE
CERTIFICATE OF CORRECTION

PATENT NO. : 7,291,737 B2  
APPLICATION NO. : 10/986352  
DATED : November 6, 2007  
INVENTOR(S) : Michael J. Kuhar et al.

Page 4 of 7

It is certified that error appears in the above-identified patent and that said Letters Patent is hereby corrected as shown below:

Column 11, lines 45-49, " 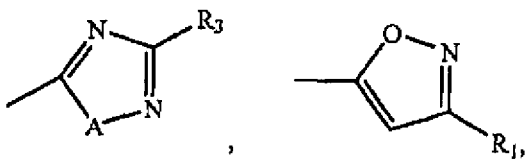 "

should read -- 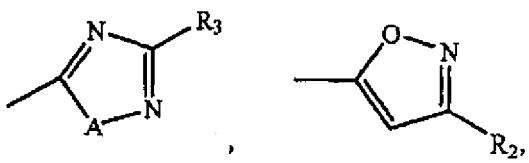 --.

| | |
|---|---|
| Column 13, line 66, "4027.87 ± 380.70" | should read -- 4,027.87 ± 380.70 --. |
| Column 15, line 11, "78 ± 2.8" | should read -- 76 ± 2.8 --; |
| line 35, "0.89 ± 0.2" | should read -- 0.69 ± 0.2 --. |
| Column 17, line 35, "0.79 ± 0.00" | should read -- 0.79 ± 0.08 --; |
| line 37, "17.90 ± 0.65" | should read -- 17.96 ± 0.85 --. |
| Column 19, line 50, "206 ± 16" | should read -- 208 ± 18 --. |
| Column 21, line 15, "5.701 ± 721" | should read -- 5,701 ± 721 --; |
| line 16, "2.076 ± 285" | should read -- 2,076 ± 285 --; |
| line 42, "2.932 ± 181" | should read -- 2,932 ± 181 --; |
| line 43, "1.476 ± 96" | should read -- 1,476 ± 96 --. |
| Column 27, line 33, "4,142.08 ± 66.07" | should read -- 4,142.08 ± 466.07 --; |
| line 66, "2,136.82 ± 208.52" | should read -- 2,138.62 ± 208.52 --. |
| Column 29, line 65, "1.36 ± 0.03" | should read -- 1.38 ± 0.03 --; |
| line 66, "36.4 ± 2.31" | should read -- 38.4 ± 2.31 --. |
| Column 37, line 37, "8.11 ± 0.67" | should read -- 6.11 ± 0.67 --; |
| line 51, "14.9 ± 1.16" | should read -- 14.9 ± 1.18 --. |

UNITED STATES PATENT AND TRADEMARK OFFICE
CERTIFICATE OF CORRECTION

PATENT NO.       : 7,291,737 B2
APPLICATION NO.  : 10/986352
DATED            : November 6, 2007
INVENTOR(S)      : Michael J. Kuhar et al.

It is certified that error appears in the above-identified patent and that said Letters Patent is hereby corrected as shown below:

Column 39, line 35, "2.246.66 ± 238.99"    should read -- 2,246.86 ± 238.99 --;
          line 53, "29.391 ± 2.324"        should read -- 29,391 ± 2,324 --;
          line 54, "35.762 ± 6.245"        should read -- 35,782 ± 6,245 --;
          line 66, "2.336 ± 176"           should read -- 2,336 ± 176 --;
          line 67, "2.955 ± 223"           should read -- 2,955 ± 223 --.

Column 41, line 12, "1.404 ± 7.1"          should read -- 1,404 ± 7.1 --;
          line 13, "776 ± 21"              should read -- 778 ± 21 --;
          line 24, "6.090 ± 468"           should read -- 6,090 ± 488 --;
          line 25, "1.926 ± 36"            should read -- 1,926 ± 38 --;
          line 48, "40.615 ± 9.416"        should read -- 40,615 ± 9,416 --;
          line 49, "6.965 ± 635"           should read -- 6,985 ± 635 --;
          line 57, "24,471 ± 1.515"        should read -- 24,471 ± 1,515 --;
          line 66, "33.085 ± 5.434"        should read -- 33,085 ± 5,434 --;
          line 67, "70.993 ± 3.563"        should read -- 70,993 ± 3,563 --.

Column 43, line 11, "2.584 ± 799"          should read -- 2,584 ± 799 --;
          line 22, "3.824 ± 418"           should read -- 3,824 ± 418 --;
          line 32, "195 ± 4.6"             should read -- 195 ± 4.8 --.

Column 47, line 26, "5.109.72 ± 187.101"   should read -- 5,109.72 ± 187.101 --.

Column 51, line 37, "409 ± 0.44"           should read -- 4.09 ± 0.44 --;
          line 50, "36,842 ± 3016"         should read -- 36,842 ± 3616 --.

Column 55, line 65, "or3β-(4-Methylphenyl)-tropane-2β-car-"
          should read -- or 3β-(4-Methylphenyl)-tropane-2β-car- --.

Column 56, line 20, "of gas has ceased."   should read -- of gas had ceased. --.

Column 57, line 4, "[α]$_D$+33.060"        should read -- [α]$_D$+33.06° --;
          line 35, "3.69 (d of d,J=y 2.6, 12 Hz, 1H),"
              should read -- 3.69 (d of d,J=2.6, 12 Hz, 1H), --;
          line 38, "Anal clacd. for"       should read -- Anal calcd for --;
          line 61, "The-oxadiazole was converted into hydrochloride salt:"
              should read -- The oxadiazole was converted into hydrochloride salt: --;
          line 65, "clacd. for" should read -- calcd for --.

UNITED STATES PATENT AND TRADEMARK OFFICE
CERTIFICATE OF CORRECTION

PATENT NO. : 7,291,737 B2
APPLICATION NO. : 10/986352
DATED : November 6, 2007
INVENTOR(S) : Michael J. Kuhar et al.

It is certified that error appears in the above-identified patent and that said Letters Patent is hereby corrected as shown below:

Column 58, line 32, "139.27, 168-29," should read -- 139.27, 168.29, --;
    lines 39-40, "clacd. for $C_{22}H_{23}CI_2N_3S.0.75H_2O$; C, 59.26; H, 5.54; N 9.42;"
        should read -- calcd for $C_{22}H_{23}CI_2N_3S.0.74H_2O$; C, 59.26; H, 5.54; N, 9.42; --;
    line 41, "Cl, 15.99; S 7.09;" should read -- Cl, 15.99; S, 7.09; --;
    line 55, "pure N-([3β-(4-Methylphenyl)"
        should read -- pure N-[3β-(4-Methylphenyl) --;
    line 61, "3385, 30451, 1625," should read -- 3385, 3045, 1625, --.

Column 59, line 13, "Anal clacd. for" should read -- Anal calcd for --;
    line 57, "Cl, 6.54. found: C, 59.78;"
        should read -- Cl, 6.54. Found: C, 59.78; --.

Column 60, line 22, "Anal clacd. for" should read -- Anal calcd for --;
    line 54, "Anal clacd. for" should read -- Anal calcd for --;
    line 56, "$[α]_D+27.430$" should read -- $[α]_D+27.43°$ --.

Column 61, line 16, "Anal clacd. for" should read -- Anal calcd for --;
    line 19, "$[α]_D$-1 72.49° (c 0.28; MeOH)."
        should read -- $[α]_D$-172.49° (c, 0.28; MeOH).
    line 43, "Anal clacd. for" should read -- Anal calcd for --;
    line 45, "22.82. found: C, 58.22;"
        should read -- 22.82. Found: C, 58.22; --;
    line 65, "Anal clacd. for" should read -- Anal calcd for --;
    line 67, "$[α]_D$-76.40 (c, 0.5; MeOH)."
        should read -- $[α]_D$-76.4° (c, 0.5; MeOH). --.

Column 62, line 17, "Anal clacd. for" should read -- Anal calcd for --.

Column 63, line 2, "Anal clacd. for" should read -- Anal calcd for --;
    line 10, "Anal clacd. for" should read -- Anal calcd for --;
    line 11, "Found: c, 60.98;" should read -- Found: C, 60.98; --;
    line 32, "Anal clacd. for" should read -- Anal calcd for --;
    line 33, "found: C, 68.65;" should read -- Found: C, 68.65; --;
    line 34, "(c, 0.71; MEOH)." should read -- (c, 0.71; MeOH). --;
    line 56, "$[α]_D$-94.570 (c, 0.39; MeOH)."
        should read -- $[α]_D$-94.57° (c, 0.39; MeOH). --.

UNITED STATES PATENT AND TRADEMARK OFFICE
CERTIFICATE OF CORRECTION

PATENT NO. : 7,291,737 B2
APPLICATION NO. : 10/986352
DATED : November 6, 2007
INVENTOR(S) : Michael J. Kuhar et al.

It is certified that error appears in the above-identified patent and that said Letters Patent is hereby corrected as shown below:

Column 64, line 11, "Anal clacd. for" should read -- Anal calcd for --;
line 12, "N 6.67;" should read -- N, 6.67; --;
line 33, "$cm^{-1}$" should read -- $cm^{-1}$. --;
line 38, "Anal clacd. for" should read -- Anal calcd for --;
line 56, "(s, 3H) 3.22" should read -- (s, 3H), 3.22 --;
line 59, "1005 $cm^{-1}$" should read -- 1005 $cm^{-1}$. --;
line 65, "Anal clacd. for" should read -- Anal calcd for --.

Column 65, line 25, "[$^3$H]-WIN 35.428" should read -- [$^3$H]-WIN 35,428 --.

Column 67, line 23, "1.00 ± 0.39" should read -- 1.06 ± 0.39 --;
line 55, "43.8 ± 8.4" should read -- 43.8 ± 6.4 --;
line 60, "3070 ± 206" should read -- 3070 ± 208 --;
line 61, ">100,00" should read -- >100,000 --.

Column 69, line 16, "[$^3$H]-WIN 35.428" should read -- [$^3$H]-WIN 35,428 --;
line 18, "124 ± 356" should read -- 124 ± 3.56 --;

Column 70, line 33, "which is in the form an HCl"
should read -- which is in the form of a HCl --.

Signed and Sealed this

Twenty-sixth Day of May, 2009

JOHN DOLL
*Acting Director of the United States Patent and Trademark Office*